(12) United States Patent
Ogawa et al.

(10) Patent No.: US 7,007,327 B2
(45) Date of Patent: Mar. 7, 2006

(54) ADJUSTABLE BED

(75) Inventors: Atsushi Ogawa, Kyoto (JP); Hideo Kawakami, Hirakata (JP); Yoshihisa Fujiwara, Uji (JP); Hidetaka Sakai, Katano (JP)

(73) Assignee: Sanyo Electric Co., Ltd., Osaka (JP)

( * ) Notice: Subject to any disclaimer, the term of this patent is extended or adjusted under 35 U.S.C. 154(b) by 47 days.

(21) Appl. No.: 10/659,150

(22) Filed: Sep. 10, 2003

(65) Prior Publication Data

US 2004/0103475 A1 Jun. 3, 2004

(30) Foreign Application Priority Data

| Sep. 11, 2002 | (JP) | ............................. 2002-265940 |
| Sep. 8, 2003 | (JP) | ............................. 2003-315736 |

(51) Int. Cl.
*A61G 7/015* (2006.01)
*A61G 7/043* (2006.01)
*A61G 7/057* (2006.01)

(52) U.S. Cl. .................................. 5/609; 5/616; 5/619
(58) Field of Classification Search ................... 5/600, 5/607, 608, 942, 613, 614, 615, 616, 619, 5/715, 609; 128/845, 848; 602/902
See application file for complete search history.

(56) References Cited

U.S. PATENT DOCUMENTS

| 3,998,209 | A | * | 12/1976 | Macvaugh | 128/848 |
| 4,228,806 | A | * | 10/1980 | Lidow | 600/544 |
| 4,287,620 | A | * | 9/1981 | Zur | 5/615 |
| 4,862,530 | A | * | 9/1989 | Chen | 5/616 |
| 5,187,657 | A | * | 2/1993 | Forbes | 600/513 |
| 5,335,657 | A | * | 8/1994 | Terry et al. | 607/45 |
| 5,655,241 | A | * | 8/1997 | Higgins et al. | 5/737 |
| 5,826,579 | A | * | 10/1998 | Remmers et al. | 128/848 |
| 5,948,303 | A | * | 9/1999 | Larson | 219/486 |
| 5,966,762 | A | * | 10/1999 | Wu | 5/715 |
| 5,999,846 | A | * | 12/1999 | Pardey et al. | 600/544 |
| 6,154,900 | A | * | 12/2000 | Shaw | 5/715 |
| 6,155,976 | A | * | 12/2000 | Sackner et al. | 600/300 |
| 6,353,950 | B1 | * | 3/2002 | Bartlett et al. | 5/617 |
| 6,575,895 | B1 | * | 6/2003 | Blair | 600/27 |

* cited by examiner

*Primary Examiner*—Michael Safavi

(57) ABSTRACT

To provide an adjustable bed that assists a user to turn comfortably in his or her sleep without mental stress. Once an automatic mode starts, measurement on the depth of sleep of the user lying on the bed is launched. The depth of sleep is measured by detecting biological information such as brain waves, heart rate, and respiratory rate of the user using electrode sensors or the like, and analyzing the biological information according to a polysomnography method or the like. If the depth of sleep is 0, i.e., the user is in REM sleep, and if one hour or more has passed since the measurement is launched or since an immediately preceding turn operation, a turn operation is performed to turn the user.

8 Claims, 19 Drawing Sheets

FIG.14
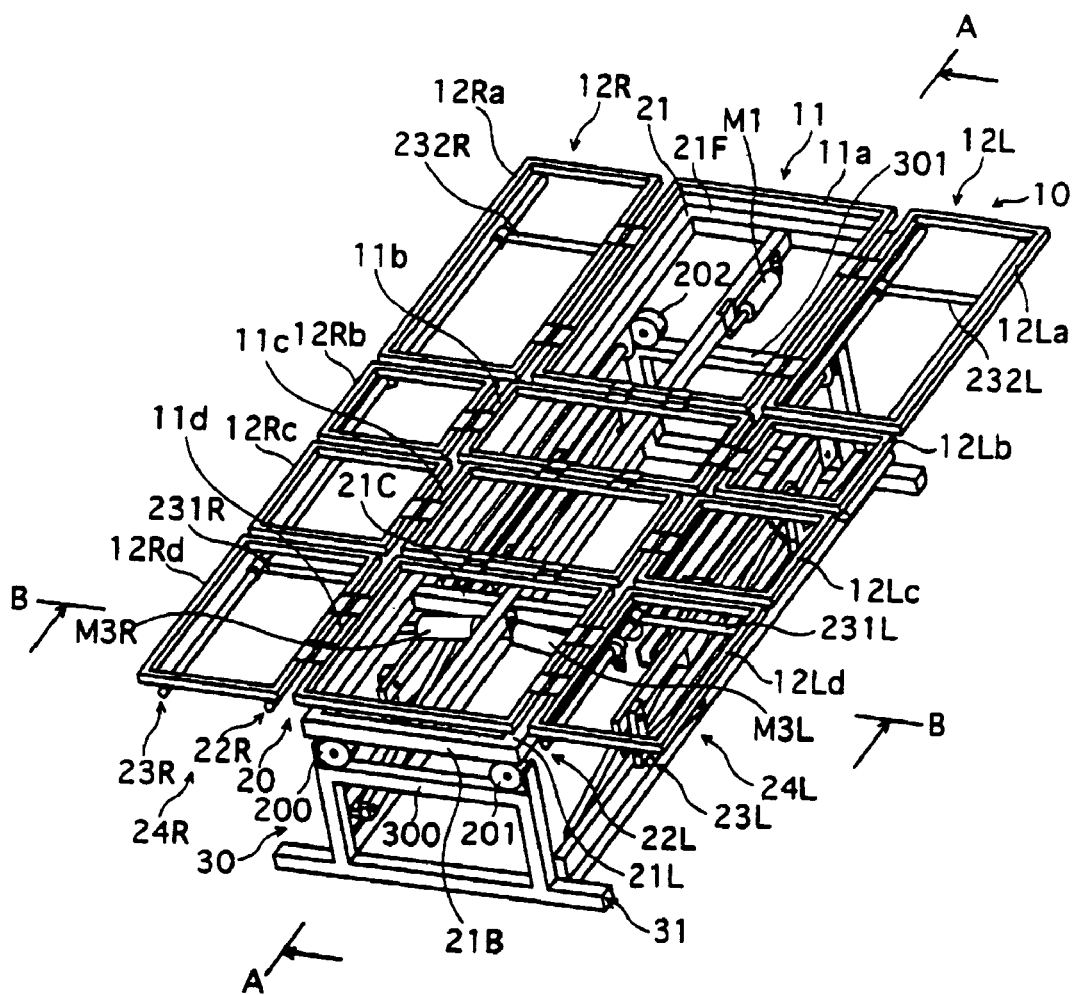
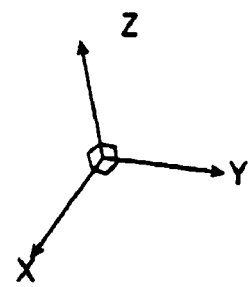

SUPINE (FLAT)

UPPER BODY RAISED

UPPER BODY RAISED / KNEES BENT UP / RIGHT SECTION RAISED

RIGHT-SIDE TURN

ADJUSTABLE BED

This application is based on an application No. 2002-265940 filed in Japan, the contents of which are hereby incorporated by reference.

BACKGROUND OF THE INVENTION

1. Field of the Invention

The present invention relates to adjustable beds used for nursing care, apnea syndrome treatment, and the like. In particular, the invention relates to improvements in control of operations of turning a cared-for person who is lying in bed during his or her sleep.

2. Related Art

To prevent the user such as a cared-for person from developing decubitus ulcers (i.e. bedsores), a typical adjustable bed used as a turn assisting bed tilts one part of or the entire surface of the mattress on which the user is lying, to assist the user to turn in the tilt direction and thereby change his or her position. Such an adjustable bed employs a mechanism of tilting the mattress from a horizontal position toward one of the left and right sides (in a lateral direction) (see Unexamined Japanese Patent Application Publication No. H06-14824 as one example).

Conventionally, timings with which the user is turned in his or her sleep are controlled by setting a timer before the user falls asleep so as to automatically tilt the mattress at, for example, two-hour intervals.

According to this conventional method of mechanically setting turn timings using a timer, however, there may be a possibility that the user is forced to turn even when his or her body does not really need such an action. This causes the user to suffer mental stress unknowingly, as a result of which his or her sleep may be disturbed.

SUMMARY OF THE INVENTION

In view of the above problem, the present invention aims to provide an adjustable bed that assists the user to turn during sleep without causing mental stress.

The stated object can be achieved by an adjustable bed including: a bed section; a tilt unit operable to perform an operation of tilting the bed section laterally; a judgment unit operable to judge which sleep stage a person who is lying on the bed section is in; and a control unit operable to control the tilt unit based on a result of the judgment by the judgment unit.

According to this construction, the judgment unit judges which sleep stage the user lying on the bed section is in, and the control unit controls the tilt unit based on the judgment result. As a result, the bed section is tilted at appropriate times in accordance with the sleep stage of the user. This allows the user to turn during sleep with no mental stress. Thus, the adjustable bed produces an excellent effect of turning the user to prevent bedsores, without interfering with the user's sleep.

Here, the judgment unit may judge whether the person is in REM sleep or not, wherein the control unit has the tilt unit perform the tilt operation, if the judgment unit judges that the person is in REM sleep.

In general, people tend to turn over when they are in REM sleep. Accordingly, by tilting the bed section when the user is in REM sleep, the user can be turned as if he or she does so spontaneously, with there being no mental stress on the part of the user.

Here, the judgment unit may judge a depth of sleep of the person, wherein the control unit has the tilt unit perform the tilt operation, if the judgment unit judges that the depth of sleep is substantially great where the person is in slow wave sleep.

When the depth of sleep is substantially great (where the user is in slow wave sleep (hereafter "SWS")), the user is almost completely unconscious. Accordingly, by tilting the bed section in SWS, the user can be turned without being aware of the motion of the bed section. Also, by tilting the bed section both when the user is in REM sleep and when the user is in SWS, the user can be turned as if he or she does so spontaneously.

Here, the control unit may prohibit the tilt unit from performing the tilt operation within a predetermined time period from completion of an immediately preceding tilt operation, irrespective of which sleep stage the person is in.

According to this construction, the user can be turned with appropriate time intervals.

BRIEF DESCRIPTION OF THE DRAWINGS

These and other objects, advantages and features of the invention will become apparent from the following description thereof taken in conjunction with the accompanying drawings which illustrate a specific embodiment of the invention.

In the drawings:

FIG. 14 is a perspective view of constructions of a bed frame, a movable stage, and a fixed stage in the bed body;

DESCRIPTION OF THE PREFERRED EMBODIMENT

The following describes an embodiment where an adjustable bed of the present invention is used as a turn assisting bed, with reference to drawings.

(Overall Construction)

Figure 1:
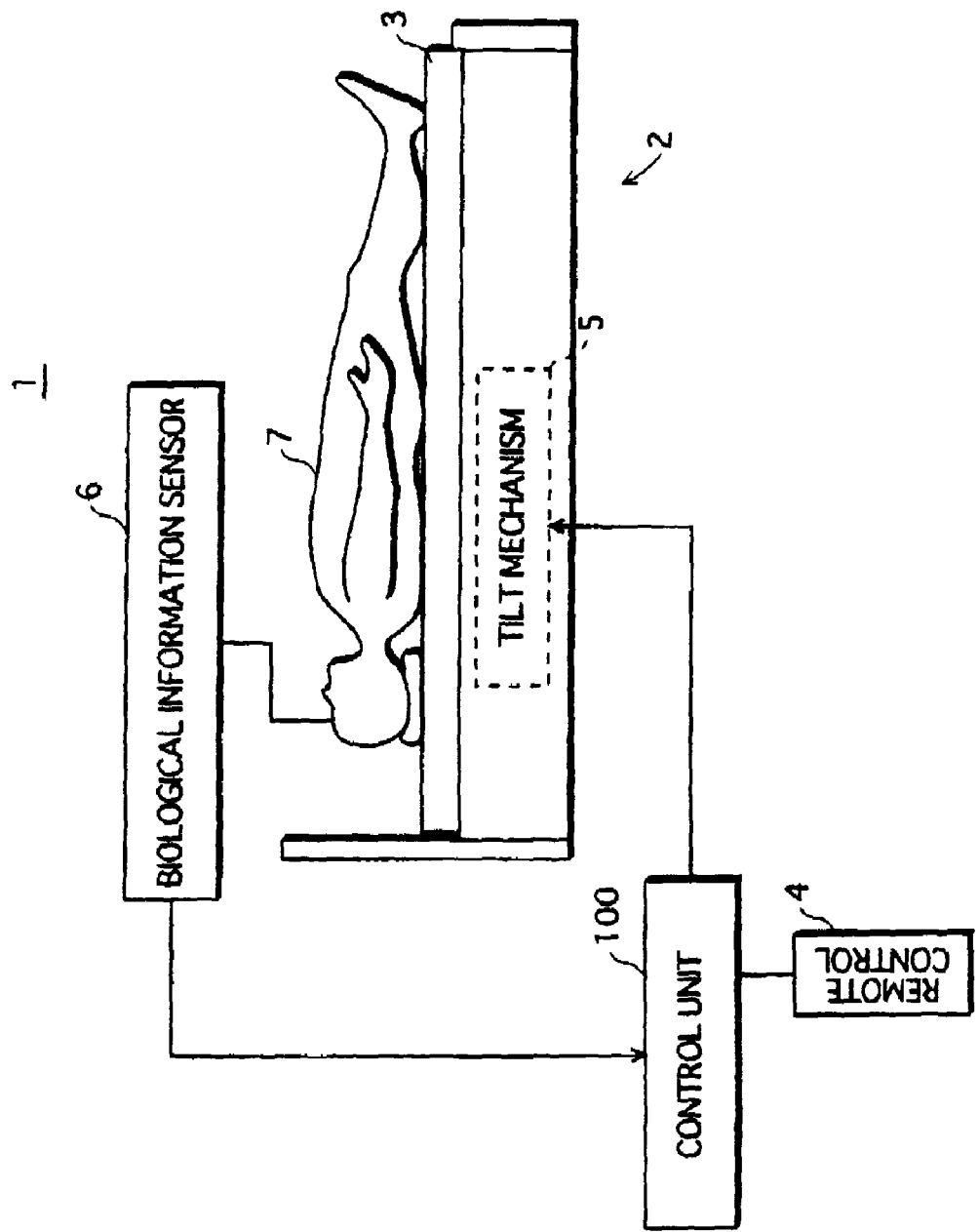
FIG. 1 shows an overall construction of a turn assisting bed.

FIG. 1 is a schematic view of an overall construction of a turn assisting bed (hereafter simply referred to as a "bed") 1 to which this embodiment relates.

In the drawing, the bed 1 is roughly made up of a bed body 2, a biological information sensor 6, and a control unit 100.

The bed body 2 includes a tilt mechanism 5. The tilt mechanism 5 is situated beneath a mattress 3 which is placed on the top of the bed body 2 (i.e. a bed surface 13 shown in FIG. 14), and bends and/or tilts the bed surface 13. When a user (e.g. a cared-for person) 7 manipulates buttons on a remote control 4, movements such as raising the upper body from a supine position, bending the knees up, and changing from a supine position to a lateral position are carried out through the tilt mechanism 5.

Figure 2:
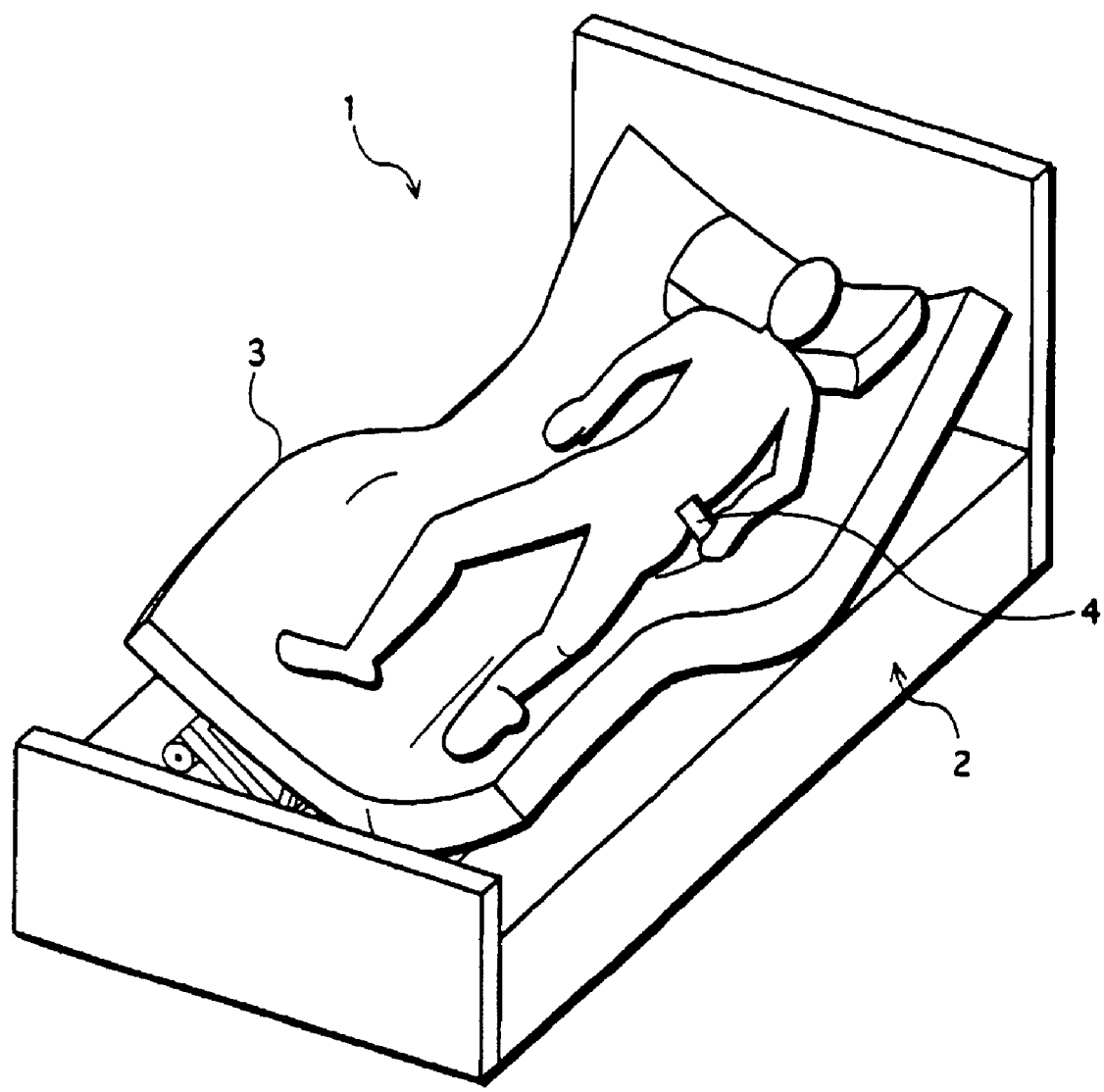
FIG. 2 is a perspective view of a bed body when the user is being turned on his or her left side.

FIG. 2 shows a situation when the user 7 is about to turn on his or her left side in a state where the upper body is raised and the knees are bent up. In this embodiment, when the bed surface 13 is tilted to change the sleep posture of the user 7 to a lateral position, a lowering side of the bed surface 13 is raised to prevent the user 7 from falling off the bed 1. In the example shown in FIG. 2, the left side is raised as viewed from the user 7. A specific construction of the bed body 2 to achieve such movements is explained in detail later.

The biological information sensor 6 detects biological information, such as brain waves, heart rate, respiratory rate, eye movement, and body movement, of the user 7 who is lying on the mattress 3. In this embodiment, a plurality of electrode sensors are used as the biological information sensor 6. These electrode sensors are attached directly to the body of the user 7 at predetermined locations such as the scalp, the outer edge of the eyelids, and the chest, using an adhesive tape or the like.

The control unit 100 judges a stage of sleep the user 7 is in, based on a detection signal output from the biological information sensor 6. When the user 7 is in REM (rapid eye movement) sleep, the control unit 100 controls the tilt mechanism 5 to perform an operation of turning the user 7. Though FIG. 1 shows the control unit 100 as being separated from the bed body 2 for ease of explanation, actually the control unit 100 is installed at the bottom of the bed body 2 so as not to be seen from outside. The control unit 100 can be manipulated either by taking it out of the installed position or by using the remote control 4.

Figure 3:
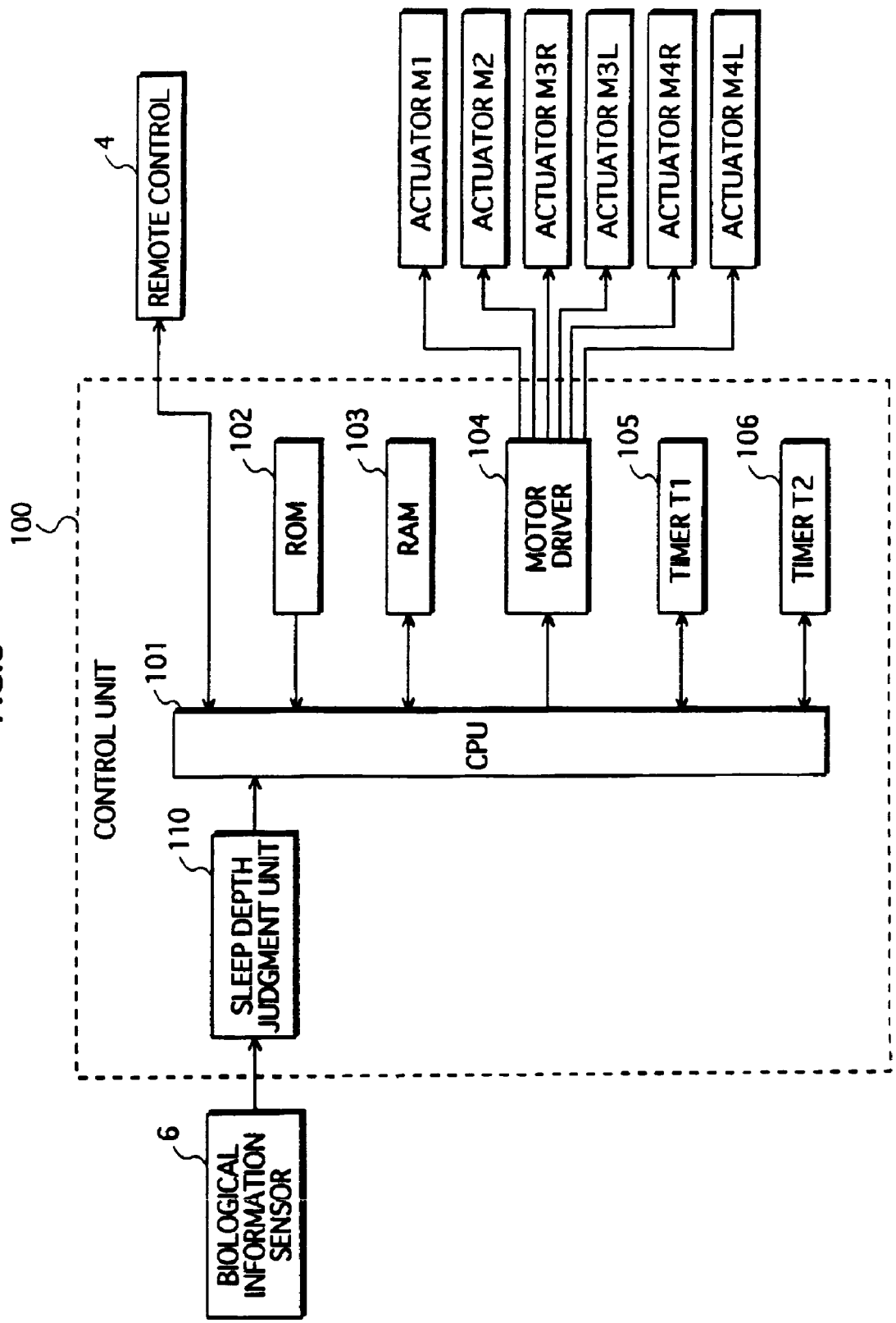
FIG. 3 is a block diagram of a construction of a control unit shown in FIG. 1.

FIG. 3 is a block diagram of a construction of the control unit 100.

In the drawing, the control unit 100 includes a sleep depth judgment unit 110, a CPU 101, a ROM 102, a RAM 103, a motor driver 104, a timer T1 105, and a timer T2 106.

The CPU 101 receives an input operation made by the user 7 or a caregiver through the remote control 4, and operates in a user-designated mode. If the user 7 or the caregiver designates an operation time (e.g. six hours) through the remote control 4, the CPU 100 operates in the designated mode for the designated time.

The ROM 102 stores a program executed by the CPU 101.

The RAM 103 temporarily stores information showing the user-designated mode and various control variables and flags. The RAM 103 also provides a work area when the CPU 101 executes the program stored in the ROM 102.

The motor driver 104 drives actuators which are equipped in the tilt mechanism 5. As described later, the tilt mechanism 5 has six actuators M1, M2, M3R, M3L, M4R, and M4L. Each actuator has a rod that is extended/compressed by turning a ball screw using a direct-current servomotor. The motor driver 104 controls these actuators to perform a turn operation.

Which is to say, the motor driver 104 drives a necessary actuator based on instructions from the CPU 101 as to which actuator should be driven, whether a rod should be extended or compressed, and a rotation speed of a servomotor, to perform a turn operation.

Each actuator includes an encoder which outputs a pulse signal showing an rpm (revolutions per minute) of a servomotor to the motor driver 104. The motor driver 104 rotates the servomotor at a fixed speed based on the pulse signal.

The CPU 101 receives the pulse signal via the motor driver 104. The CPU 101 calculates an amount of extension of a rod of the actuator based on the pulse signal. Thus, the CPU 101 monitors to what extent the bed surface 13 is bent or tilted with reference to a flat, horizontal position.

Take an operation of raising the upper body of the user 7 as one example. When a back bed section 11a (see FIG. 14) is raised at α° from a horizontal position (0°), the CPU 101 judges that the upper body of the user 7 has been raised. After this, when the back bed section 11a is lowered from the α° position to the 0° position, the CPU 101 judges that the upper body of the user 7 has returned to the horizontal position. The back bed section 11a referred to here is one part of a bed section 11 that corresponds to the back of the user 7. The bed section 11 is one part of a bed frame 10 on which the body of the user 7 lying on the bed 1 is normally situated. The bed frame 10 forms the bed surface 13 (see FIG. 14).

Here, a home switch which is ON when the back bed section 11a is in the horizontal position and OFF when the back bed section 11a is in a non-horizontal position may be employed. In this case, the CPU 101 judges that the upper body of the user 7 has returned to the horizontal position when the home switch becomes ON.

The timer T1 105 and the timer T2 106 are used mainly to measure time, when the CPU 101 operates in automatic mode. The timer T1 105 is reset each time one turn operation is performed, and measures time which has passed since the turn operation. The timer T2 106 measures time which has passed since the automatic mode starts.

The sleep depth judgment unit 110 judges the depth of sleep of the user 7, based on a signal output from the biological information sensor 6. In this embodiment, a known polysomnography device is used as the sleep depth judgment unit 110. A polysomnography device detects currents at predetermined parts of the body of the user 7, using the aforementioned electrode sensors as the biological information sensor 6. The polysomnography device simultaneously and continuously records physiologic variables such as brain wave activity (EEG (electroencephalogram)), eye movement (EOG (electrooculogram)), and muscle tone (EMG (electromyogram)), to analyze the depth of sleep. Since this analysis method is well known in the art, its detailed explanation has been omitted here.

Figure 4:
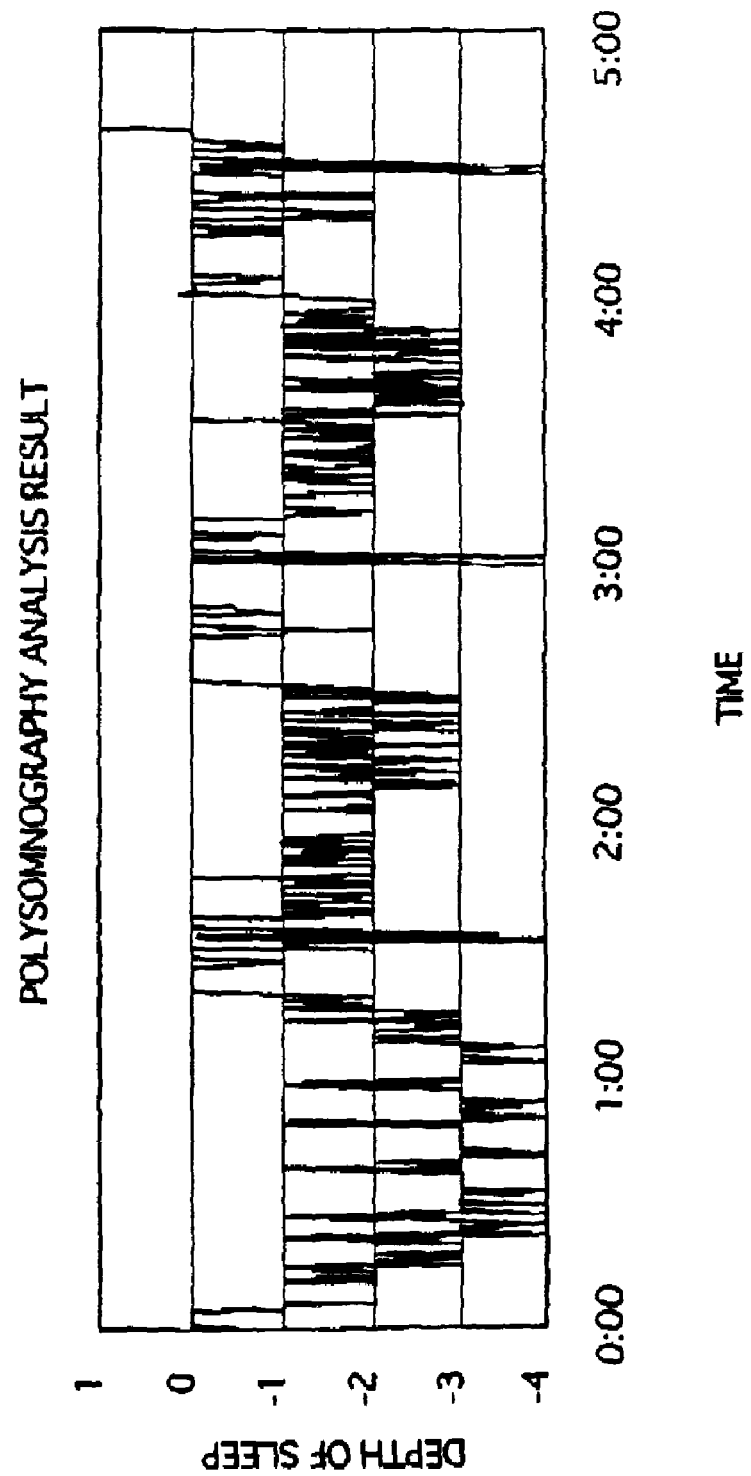
FIG. 4 is a graph showing a result of analysis on the depth of sleep by a polysomnography device.

FIG. 4 is a graph showing an example result of measuring the depth of sleep of the user 7 using the polysomnography device as the sleep depth judgment unit 110.

In the graph, the horizontal axis represents time, and the vertical axis represents the depth of sleep. Also, the depth of sleep at 4 is denoted by −4, the depth of sleep at 3 is denoted by −3, the depth of sleep at 2 is denoted by −2, and the depth of sleep at 1 is denoted by −1.

Here, the polysomnography device outputs a polysomnography analysis result such as the one shown in FIG. 4 as an electrical signal (voltage or current) Accordingly, threshold levels of electrical signals corresponding to the depths of sleep 1, 0, −1, −2, −3, and −4 are set in an internal comparator or the like beforehand, and the signal output from the polysomnography device is compared with each of these threshold levels. In this way, the depth of sleep can be judged.

In general, there are two states of sleep: REM sleep and NREM (non-rapid eye movement) sleep. REM sleep is a period during which sleep is lightest and rapid eye movements appear. NREM sleep is a period during which sleep is deeper. When the depth of sleep is −1, −2, −3, or −4, the user is in NREM sleep. When the depth of sleep is 0, the user is in REM sleep. When the depth of sleep is 1, the user is in wakefulness. As can be seen from FIG. 4, REM sleep alternates with NREM sleep approximately every 90 minutes.

Normally, REM sleep constitutes about 20 to 25% of total sleep time. REM sleep is associated with not only rapid eye movements but also faster breathing and faster pulse. Also, the blood pressure is higher than in NREM sleep. During REM sleep, vivid, complex dreams often occur and nerves become active. Therefore, people tend to turn when they are in REM sleep.

In view of this, the control unit 100 controls the tilt mechanism 5 to make the user 7 turn during REM sleep. Since the user 7 is automatically turned when his or her body needs such an action, the stress of the user 7 will be substantially reduced when compared with the conventional technique.

(Control by the Control Unit 100)

The control unit 100 controls the tilt mechanism 5 in the following manner.

Before the user 7 sleeps, the user or the caregiver attaches the biological information sensor 6 to the user 7 at the scalp, the outer edge of the eyelids, the chest, and the like. The user or the caregiver then sets the control unit 100 in automatic mode through the remote control 4, and presses a START button.

Figure 5:
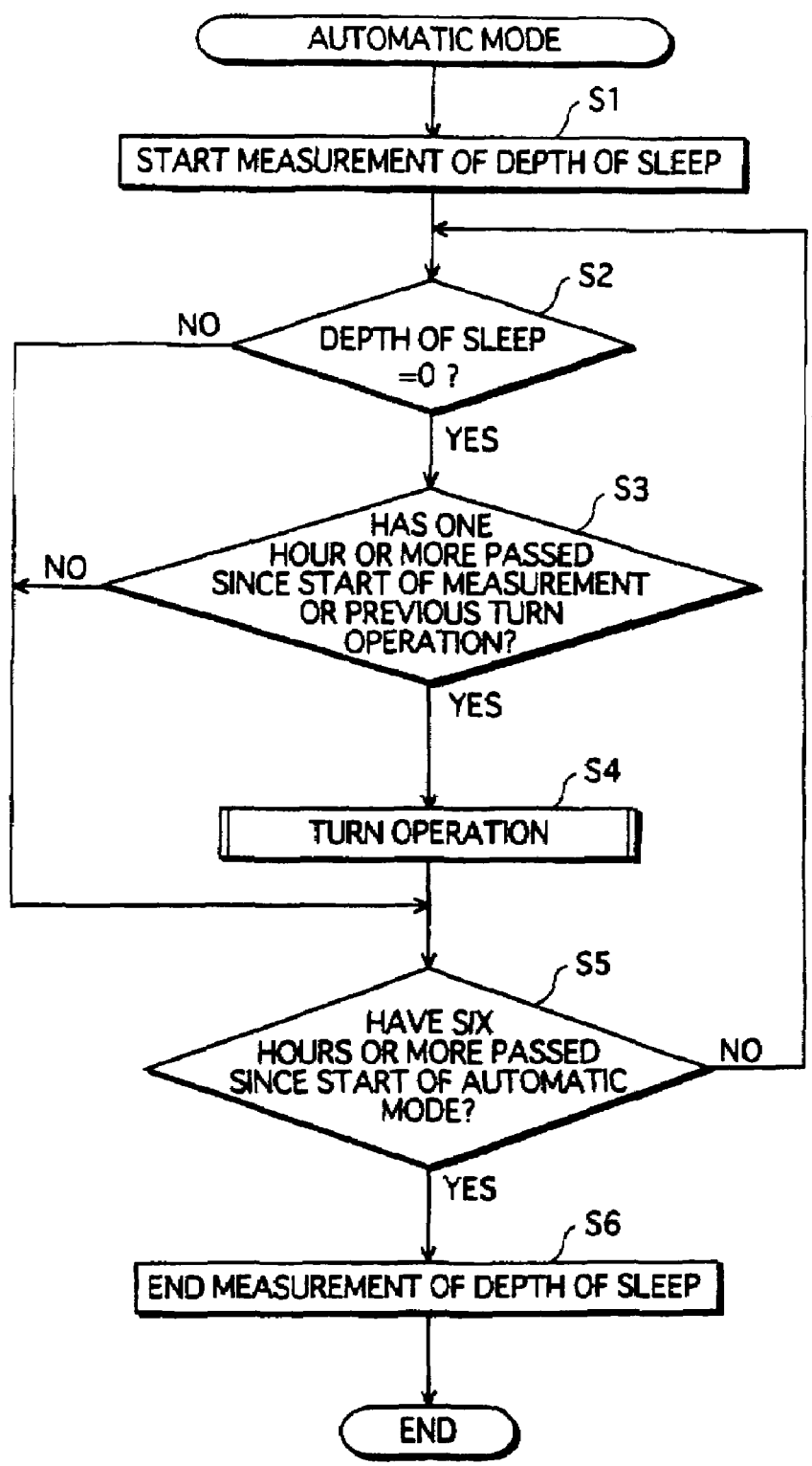
FIG. 5 is a flowchart of a control procedure performed by the control unit in automatic mode.

FIG. 5 is a flowchart of a control procedure performed by the control unit 100 in automatic mode.

The sleep depth judgment unit 110 starts measuring the depth of sleep of the user 7, based on a signal output from the biological information sensor 6 (S1).

The sleep depth judgment unit 110 judges whether the depth of sleep is 0 (S2). As explained earlier with reference to FIG. 4, if the depth of sleep is not 1, the user 7 is judged as sleeping. Also, if the depth of sleep is 0, the user 7 is judged as being in REM sleep.

If the depth of sleep is 0 (S2:YES), the CPU 101 judges the following. In the case where the user 7 has not yet been turned after he or she falls asleep, the CPU 101 judges whether one hour or more has passed since the measurement of the depth of sleep starts. Here, the CPU 101 may instead judge whether one hour or more has passed since the user falls asleep. The time when the user falls asleep can be specified as the time when the depth of sleep falls to −1 and below for the first time after the measurement of the depth of sleep starts. In the case where the user 7 has been turned after he or she falls asleep, on the other hand, the CPU 101 judges whether one hour or more has passed since an immediately preceding turn operation, by referring to the timer T1 105 (S3).

If the user 7 is frequently turned just because he or she is in REM sleep, the user 7 is likely to feel stress. Besides, if the user 7 is turned during REM sleep which occurs immediately after he or she falls asleep, the user 7 may wake up. Therefore, only when one hour or more has passed since the measurement of the depth of sleep starts (or the user 7 falls asleep) or since the immediately preceding turn operation, the procedure advances to step S4 to perform an operation of turning the user 7. Though one hour is set as a minimum time interval required between turn operations, another appropriate time period may be set as the minimum time interval in consideration of factors such as the sleep cycle and physical condition of the user 7. It is not desirable, however, to set a minimum time interval longer than 90 minutes which are a typical sleep cycle, for the following reason. If the minimum time interval required between turn operations is set greater than the sleep cycle, the user 7 who is turned in one REM sleep may not be turned in the next REM sleep. This significantly decreases the number of times the user 7 turns in his or her sleep.

Figure 6:
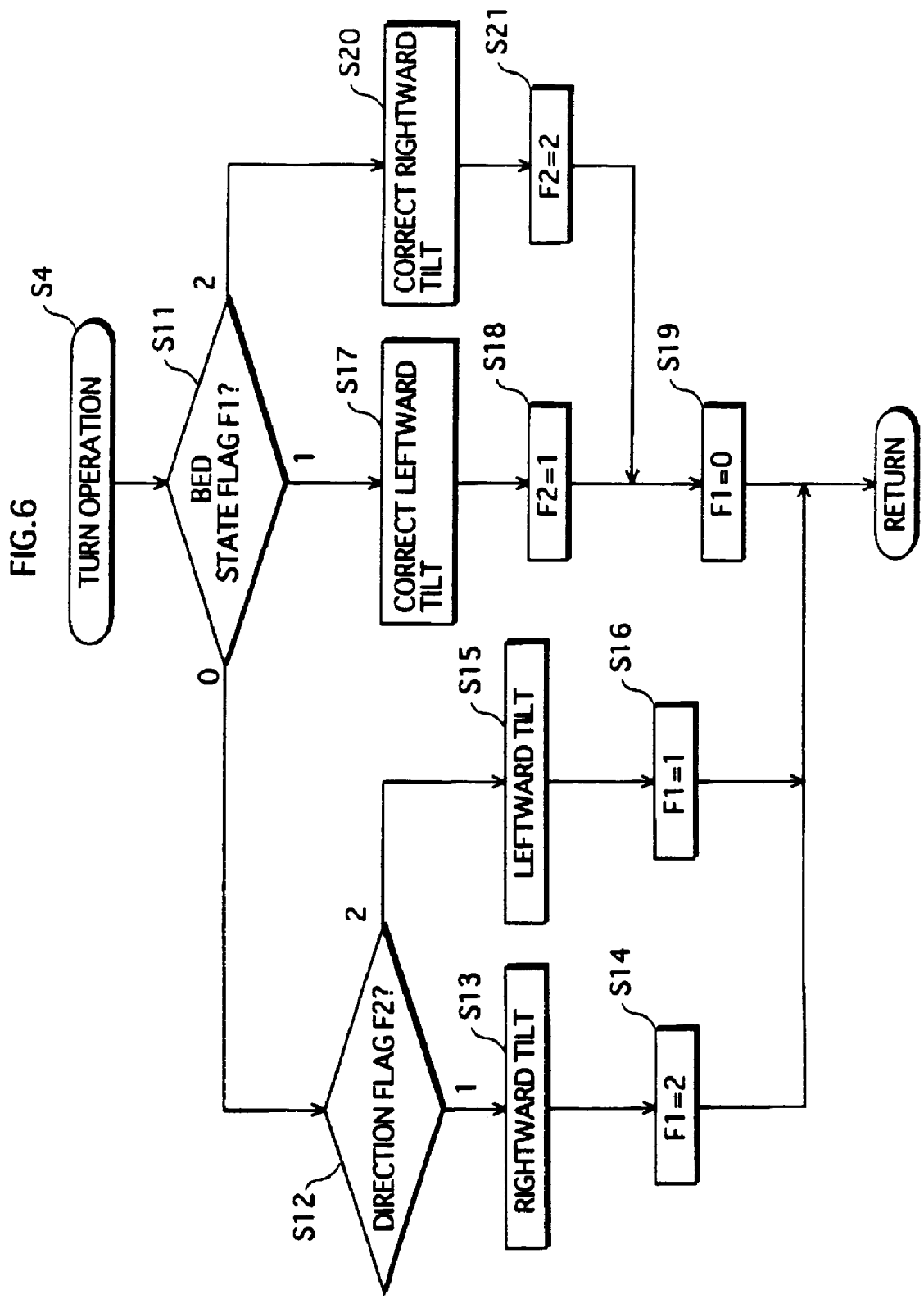
FIG. 6 is a flowchart of a turn operation shown in FIG. 5.

FIG. 6 is a flowchart of the turn operation in step S4.

In the turn operation, two flags (bed state flag F1 and direction flag F2) are used. These flags are stored in the RAM 103. When the automatic mode starts, F1=0 and F2=1 are set as initial values.

Bed state flag F1 is a flag showing the current position of the bed surface 13. When F1=0, the bed surface 13 is in a horizontal position. When F1=1, the bed surface 13 is tilted to the left at a predetermined angle. When F1=2, the bed surface 13 is tilted to the right at the predetermined angle. Here, "left" and "right" are the relative positions of the left and right sides with reference to the user 7 who is lying supine on the bed 1.

Direction flag F2 is a flag showing to which side the bed surface 13, which is currently in the horizontal position, should be tilted next. When F2=1, the bed surface 13 should be tilted to the right. When F2=2, the bed surface 13 should be tilted to the left.

The turn operation is performed as follows. The CPU 101 checks bed state flag F1 (S11). If F1=0, the bed surface 13 is currently in the horizontal position. Accordingly, the CPU 101 checks direction flag F2 (S12). If F2=1, the CPU 101 controls the tilt mechanism 5 to perform an operation of tilting the bed surface 13 to the right, to have the user 7 turn on his or her right side (S13). The CPU 101 then changes flag F1 to 2 (S14).

The tilt operation performed here is not an operation of merely tilting the bed surface 13 in a flat state to the right. Rather, in a state where the back bed section 11a and a thigh bed section 11c of the bed section 11 are raised to have the user 7's upper body elevated and knees bent up (this position is hereafter called a "bent position"), a right section 12R of the bed frame 10 is raised and then the entire bed surface 13 is tilted to the right. This allows the user 6 to turn on his or her right side in a state of being as if folded with the mattress 3. Thus, the user 7 can be turned without uneasiness or stress. This tilt operation is explained in more detail in the description of the tilt mechanism 5 later.

If F2=2 in step S12, the CPU 101 controls the tilt mechanism 5 to perform an operation of tilting the bed surface 13 to the left (S15). The CPU 101 then changes direction flag F1 to 1 (S16), and proceeds to step S5 in FIG. 5.

If F1=1 in step 311, the bed surface 13 is currently tilted to the left. Accordingly, the CPU 101 controls the tilt mechanism 5 to tilt the bed surface 13 to the right to recover the horizontal position (S17), and sets direction flag F2 to 1 (S18).

If F1=2 in step S11, the bed surface 13 is currently tilted to the right. Accordingly, the CPU 101 controls the tilt mechanism 5 to tilt the bed surface 13 to the left to recover the horizontal position (S20), and sets direction flag F2 to 2 (S21).

After step S18 or S21, the CPU 101 changes bed state flag F1 to 0 which indicates that the bed surface 13 is in the horizontal position (S19), and proceeds to step S5 in FIG. 5.

When step 34 is repeated in the above way, the bed surface 13 undergoes a change such as horizontal position→rightward tilt→horizontal position→leftward tilt→horizontal position→rightward tilt. . . . As a result, the user 7 undergoes a change such as supine position→right lateral position→supine position→left lateral position→supine position→right lateral position . . . . Here, the same position is maintained for at least one hour, since the lapse of one hour as the minimum time interval between turn operations is monitored in step S3. Given that REM sleep occurs at intervals of about 90 minutes, the same position is maintained for approximately 90 minutes.

Note that the order in which the position of the user 7 is changed is not limited to the above. For example, the user 7 may undergo such a change as supine position→left lateral position→right lateral position→supine position→left lateral position . . . . Also, a plurality of orders in which the position of the user 7 is changed may be stored in an internal memory beforehand. In this case, the user or the caregiver selects one of the orders using the remote control 4, when setting the automatic mode.

After step S4, the CPU 101 checks the timer T2 106 to judge whether six hours or more have passed from when the automatic mode starts (S5). If six hours or more have not passed yet (S5:NO), steps S2 to S4 are repeated. If six hours or more have already passed (S5:YES), the measurement on the depth of sleep is stopped (S6) to end the automatic mode. Though a minimum time period for the automatic mode is set at six hours in this example, the minimum time period may be set freely through the remote control 4 based on an average sleep time of the user 7.

According to the above control procedure, the user 7 is turned during REM sleep which is a period of sleep when people tend to turn. Accordingly, even if the user 7 is incapable of turning on his or her own, the user 7 can be turned as if he or she does so spontaneously. This allows the user 7 to sleep restfully without uneasiness or stress.

(Modifications to the Control Procedure in Automatic Mode)

(1) Though the user 7 is turned during REM sleep according to the above control procedure, the invention is not limited to such. For example, when the depth of sleep is −3 or −4 in FIG. 4, i.e., when the depth of sleep is substantially great (where the user is in SWS), the user 7 is almost completely unconscious. In such a stage, even if the bed surface 13 is moved, the user 7 is unlikely to sense the change of his or her position and feel stress caused by such a change.

Accordingly, the above control procedure can be modified so that a turn operation is performed when the sleep of the user 7 is substantially deep (SWS).

Figure 7:
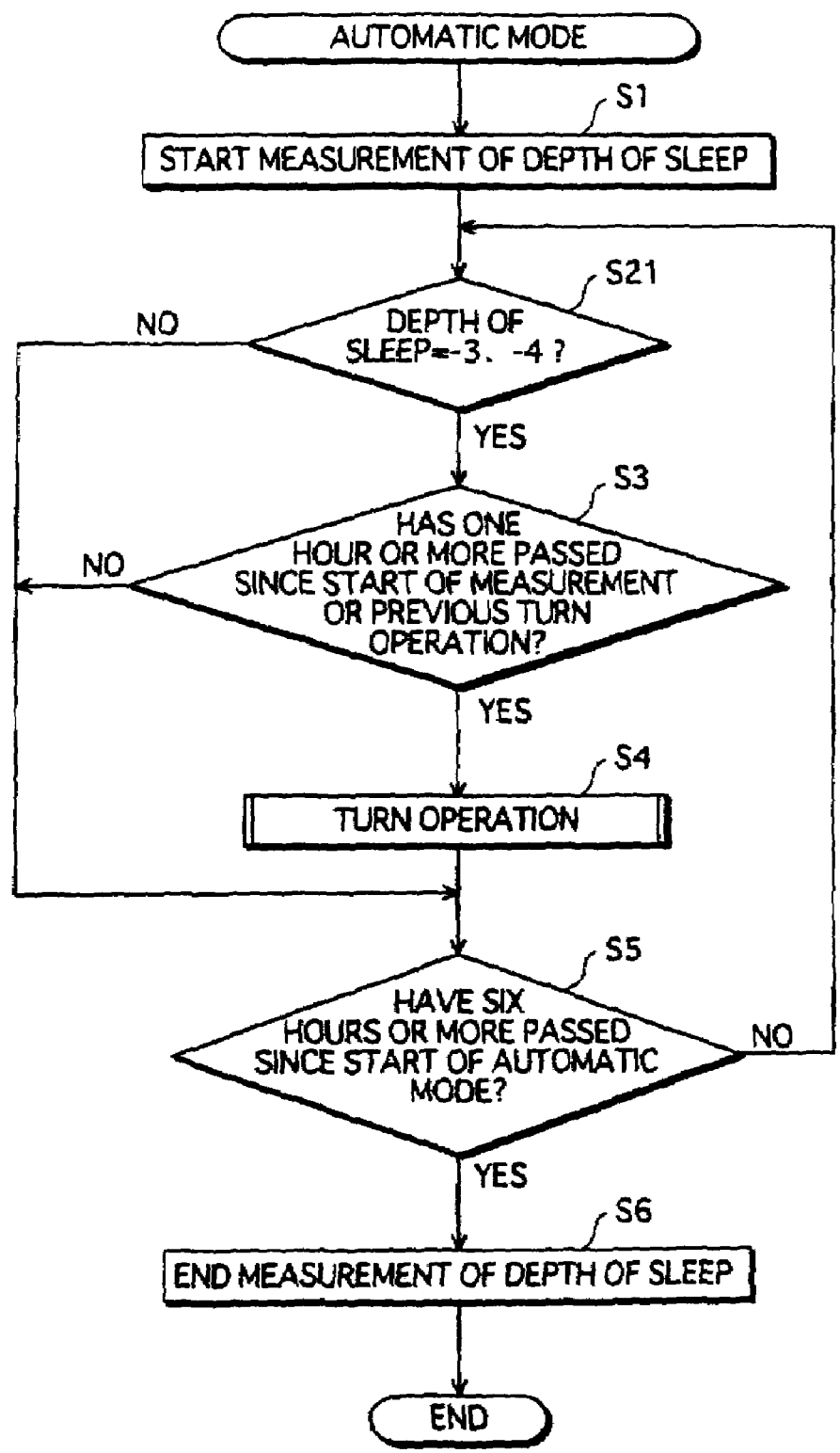
FIG. 7 is a flowchart of amodification to the control procedure performed by the control unit.
Figure 8:
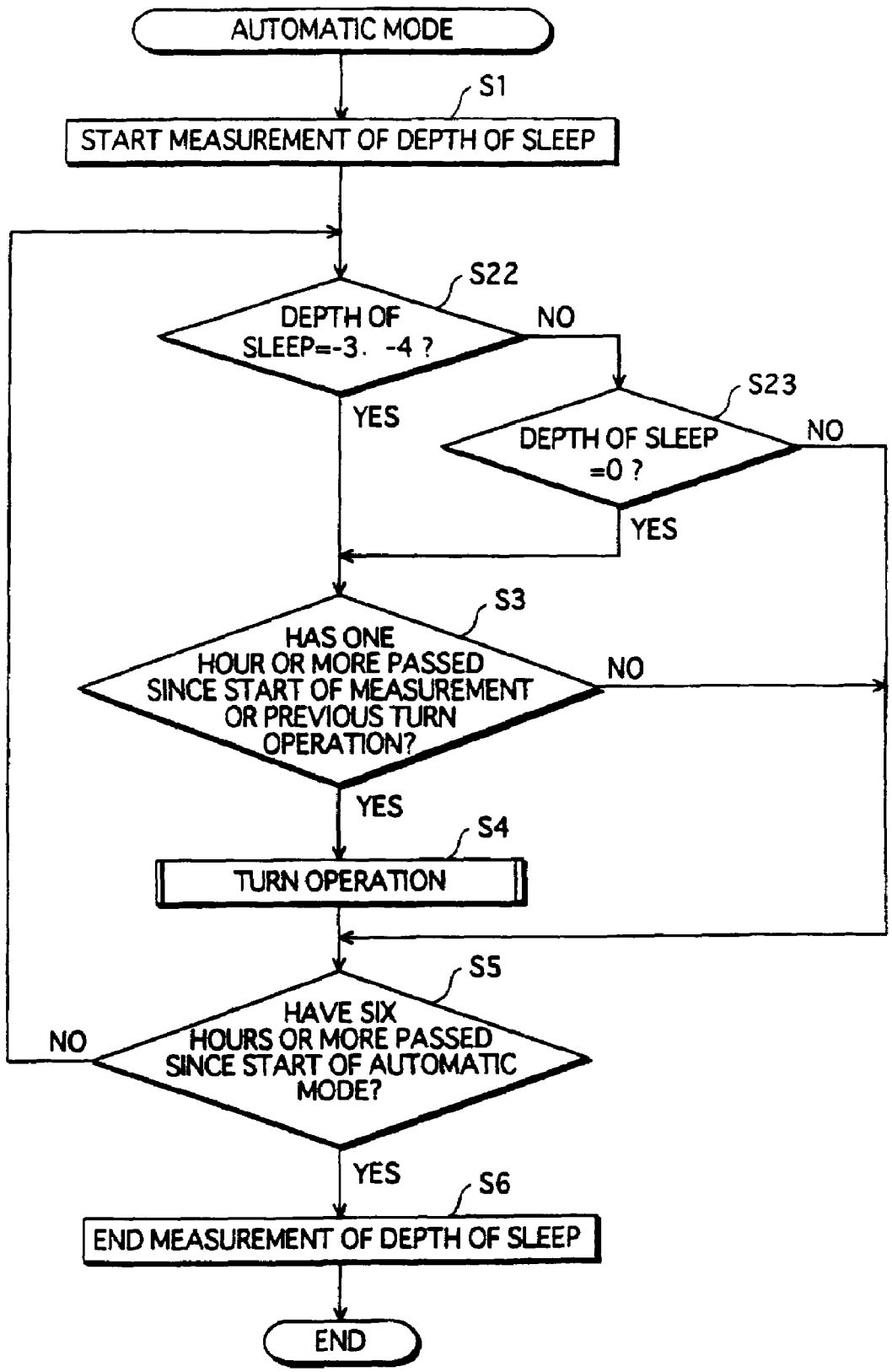
FIG. 8 is a flowchart of another modification to the control procedure performed by the control unit.

FIG. 7 is a flowchart of a control procedure performed by the control unit 100 in this case. This flowchart is different from that shown in FIG. 5 only in that step S2 has been replaced with step S21. This one of the following methods (a) and (b) may be adopted.

(a) Before ending the automatic mode, the control unit 100 judges whether the bed surface 13 is tilted. If the bed surface 13 is tilted, the control unit 100 controls the tilt mechanism 5 to return the bed surface 13 to the horizontal position, and then ends the automatic mode. When returning the bed surface 13 to the horizontal position, the user 7 may not be in REM sleep (or in the stage where the depth of sleep is substantially great) Therefore, it is desirable to move the bed surface 13 to the horizontal position as slowly as possible.

(b) The control unit 100 predicts how many turn operations will be performed before the end of the automatic mode, based on the time period set for the automatic mode (six hours in this embodiment), the sleep cycle of the user 7 (which may be either measured beforehand or uniformly set at 90 minutes), and the time when the first turn operation is performed after the user 7 falls asleep. Based on this prediction, the control unit 100 controls the order in which the position of the bed surface 13 is changed, so that the bed surface 13 returns to the horizontal position as a result of the last turn operation.

(Modification to the Biological Information Sensor 6)

In this embodiment, the biological information sensor 6 is realized by the plurality of electrode sensors which are attached directly to the body of the user 7 to detect brain waves and the like. According to this construction, however, the user 7 may feel physically restrained by multiple codes which extend from the electrode sensors to connect to the sleep depth judgment unit 110.

Also, it is inconvenient for the user 7 and the caregiver to attach a lot of electrode sensors to the body of the user 7 before the user 7 sleeps every night.

In view of this, the applicant of the present application devised a sheet-type biological information sensor (hereafter a "sheet sensor") prior to the present application. The applicant developed a device for computing the heart rate, the respiratory rate, and the number of body movements based on changes of the body pressure applied on the sheet sensor which is placed under the back of a person, and accurately estimating the depth of sleep from the computation result. The applicant filed patent applications based on this invention (Japanese Patent Applications Nos. 2002-065928 and 2002-075673).

If such a device is used in the bed 1, it is possible to estimate the depth of sleep easily and turn the user 7 comfortably based on the estimation result, with there being no burden on the part of the user 7. This enables the user 7 to have a more pleasant sleep.

The sheet sensor and a principle of measuring the depth of sleep using the sheet sensor are briefly explained below.

Figure 9:
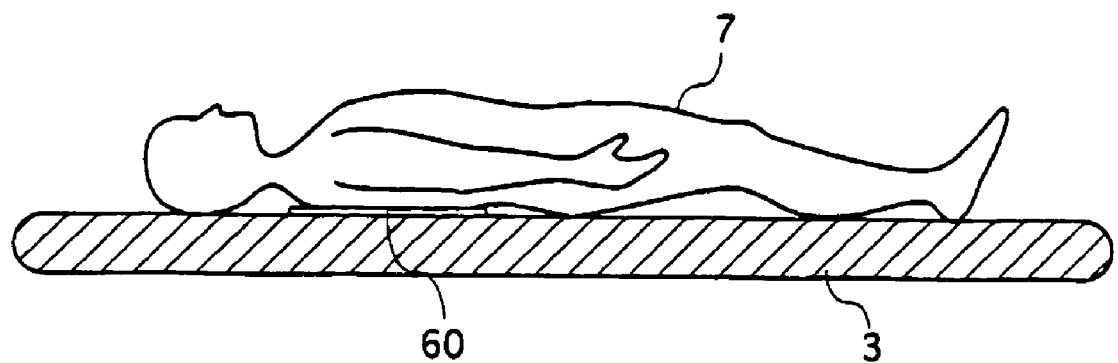
FIG. 9 shows a situation where a sheet sensor is used as a biological information sensor shown in FIG. 1.

FIG. 9 shows a situation where a sheet sensor 60 is placed under the back of the user 7.

Figure 10:
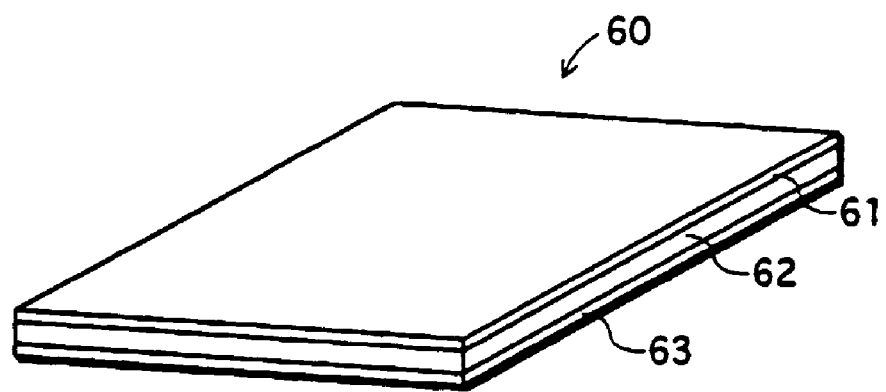
FIG. 10 is a perspective view of the sheet sensor.

FIG. 10 is a perspective view of the sheet sensor 60. As illustrated, the sheet sensor 60 has sheet electrodes 61 and 63 which are opposed to each other with a sheet insulator 62 interposed therebetween. The sheet electrodes 61 and 63 are made of copper foil or the like. The sheet insulator 62 is made of an insulating elastic material such as foamed polyurethane.

When placed under the body of the user 7, the surface of the sheet sensor 60 receives pressure and vibration caused by the heart beating and respiration of the user 7. This elastically deforms the sheet insulator 62 in the sheet sensor 60, and changes the distance between the sheet electrodes 61 and 63. As a result, the capacitance of the sheet sensor 60 changes.

Figure 11:
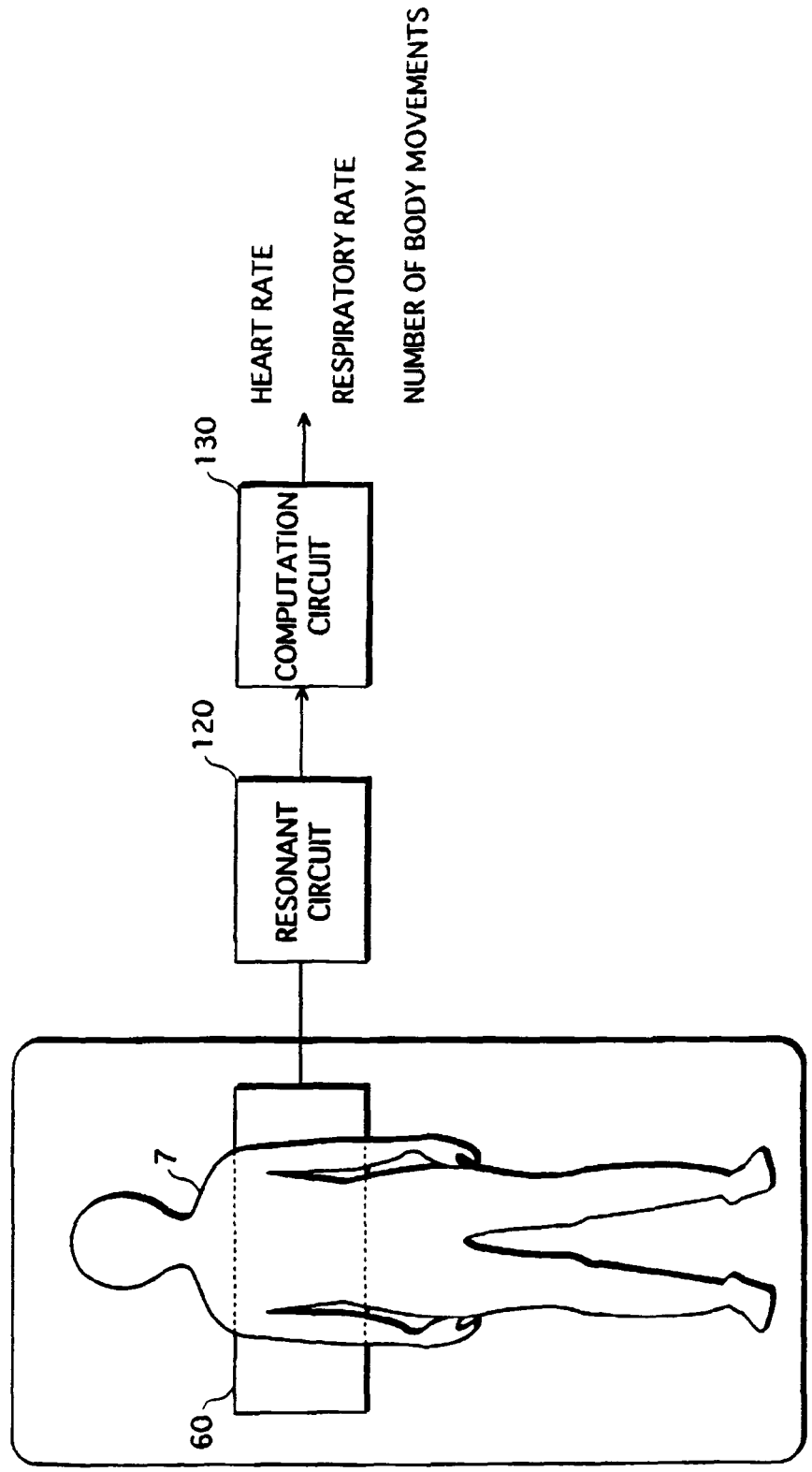
FIG. 11 is a schematic view of a construction of outputting biological information when the sheet sensor is used.

A lead wire is extended from the sheet electrodes 61 and 63 and connected to a resonant circuit 120, as shown in FIG. 11. The resonant circuit 120 includes an LC resonant circuit or a CR resonant circuit which has the sheet sensor 60 as a resonant capacitor. The oscillation frequency of the resonant circuit 120 varies as the capacitance of the sheet sensor 60 changes due to the heart beating and the respiration.

Which is to say, the change in oscillation frequency of the resonant circuit 120 contains frequency components relating to the heart beating and respiration of the user 7. This being so, a computation circuit 130 analyzes the oscillation frequency of the resonant circuit 120 to compute the heart rate, the respiratory rate, the number of body movements, and the like.

In more detail, the computation circuit 130 conducts the analysis based on differences between the heartbeat cycle, the respiration cycle, and the body movement cycle. That is to say, the computation circuit 130 performs an operation such as digital filtering on the change in oscillation frequency of the resonant circuit 120, to extract variation components relating to the heart beating, the respiration, and the body movement. The computation circuit 130 computes the heart rate, the respiratory rate, and the number of body movements based on the extracted components.

Figure 12:
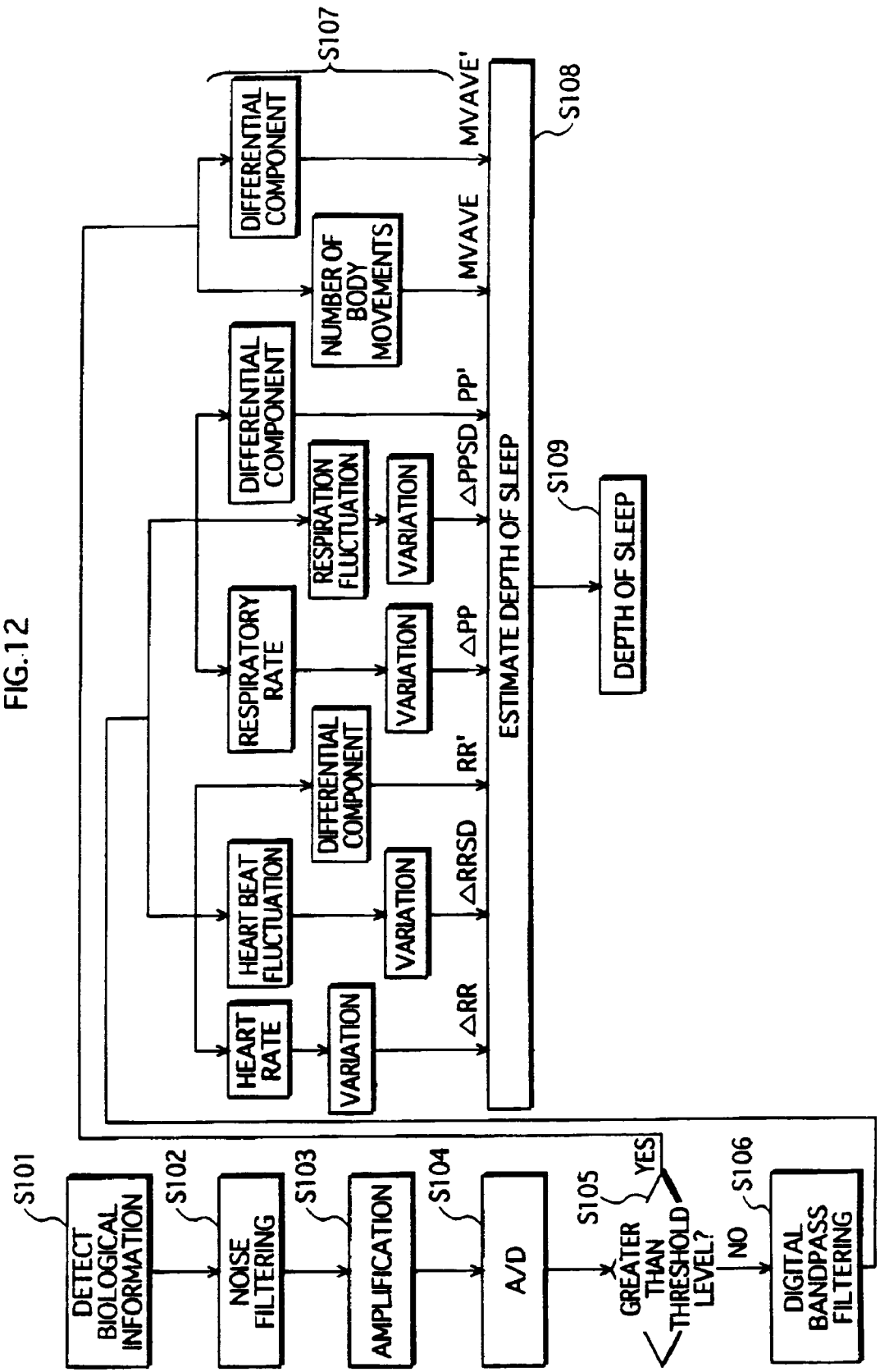
FIG. 12 is a flowchart of a procedure of estimating the depth of sleep based on biological information obtained by the construction shown in FIG. 11.

The sleep depth judgment unit 110 estimates the depth of sleep from the obtained biological information, according to a procedure shown in FIG. 12. Note that FIG. 12 shows a procedure from the biological information detection onward, for ease of explanation.

A biological information signal (a change in oscillation frequency in this example) is detected by the sheet sensor 60 and the resonant circuit 120 (S101) The biological information signal is subjected to noise filtering (S102), amplification (S103), and analog-to-digital conversion (S104).

The resulting biological information signal is compared with a predetermined threshold level, to separate data whose variation is greater than the threshold level (body movement component data) from data whose variation is no greater than the threshold level (heartbeat component data and respiration component data) (S105). The latter data is subjected to digital bandpass filtering, to separate the heartbeat component data from the respiration component data (S106).

From the heartbeat component data, heart rate detection data (RR) showing the number of heartbeats per unit time, a standard deviation (RRSD) showing a fluctuation in heart rate, and a differential value (RR') showing a differential component in heart rate are calculated (S107). Likewise, from the respiration component data, respiratory rate detection data (PP) showing the number of breaths per unit time, a standard deviation (PPSD) showing a fluctuation in respiratory rate, and a differential value (PP') showing a differential component in respiratory rate are calculated.

After this, a variation component of RR from a corresponding reference value, a variation component of RRSD from a corresponding reference value, and RR' are calculated. Also, a variation component of PP from a corresponding reference value, a variation component of PPSD from a corresponding reference value, and PP' are calculated. These calculation results are set as base data for the depth of sleep.

Here, the variation component of each of RR and PP from the corresponding reference value and the variation component of each of RRSD and PPSD from the corresponding reference value are differences, for instance, from a mean value of each of RR and PP and a mean value of each of RRSD and PPSD obtained in a past fixed time period. In other words, direct-current components of personal differences included in heart rate and respiratory rate are removed from these variation components.

Also, RR' and PP' are each obtained by calculating a difference from a heart rate and respiratory rate of a past fixed time period. In other words, alternating-current components of personal differences included in heart rate and respiratory rate are removed from these differential values.

Thus, each item of base data is obtained with personal differences corrected. By estimating the depth of sleep based on such data, it is possible to produce an accurate estimation result with personal differences corrected.

From the body movement component data, detection data (MVAVE) showing a mean value in a fixed time period and a differential component (MVAVE') in detection data are calculated. These computation results are added to the base data, with it being possible to enhance the precision in estimating the depth of sleep.

A sleep depth estimate equation has been obtained beforehand, by performing multiple regression analysis on a plurality of sets of base data of a plurality of persons. Through the use of this sleep depth estimate equation (S108), the depth of sleep is estimated from the base data obtained in step S107 (S109).

Note here that a regression operation in the multiple regression analysis is carried out in accordance with a sleep depth regression model equation which has the plurality of sets of base data of the plurality of persons as parameters.

The sleep depth regression model equation is transformed into the sleep depth estimate equation which has the eight types of base data as parameters. The depth of sleep is computed using this sleep depth estimate equation.

Though this example employs multiple regression analysis, the invention should not be limited to such. The depth of sleep can equally be computed using other methods such as discriminant analysis, fuzzy logic, neural network, and rough set analysis.

With the provision of the sheet sensor 60 having a simple construction, the depth of sleep can be estimated with high precision through the above computation. By exercising the aforedescribed control procedure based on the result of this estimation, it is possible to provide comfortable sleep to the user 7 while alleviating the burdens on the user 7.

(Construction of the Bed Body 2)

As explained earlier with reference to FIG. 2, the bed body 2 has a novel, special construction for tilting the bed surface 13 in a state where the back bed section 11a and the thigh bed section 11c are raised to assume a bent position and the right section 12R or a left section 12L is raised. This allows the user 7 to turn on his or her side in a state of being as if folded with the mattress 3. This construction of the bed body 2 and in particular the construction of the tilt mechanism 5 are explained below.

Figure 13:
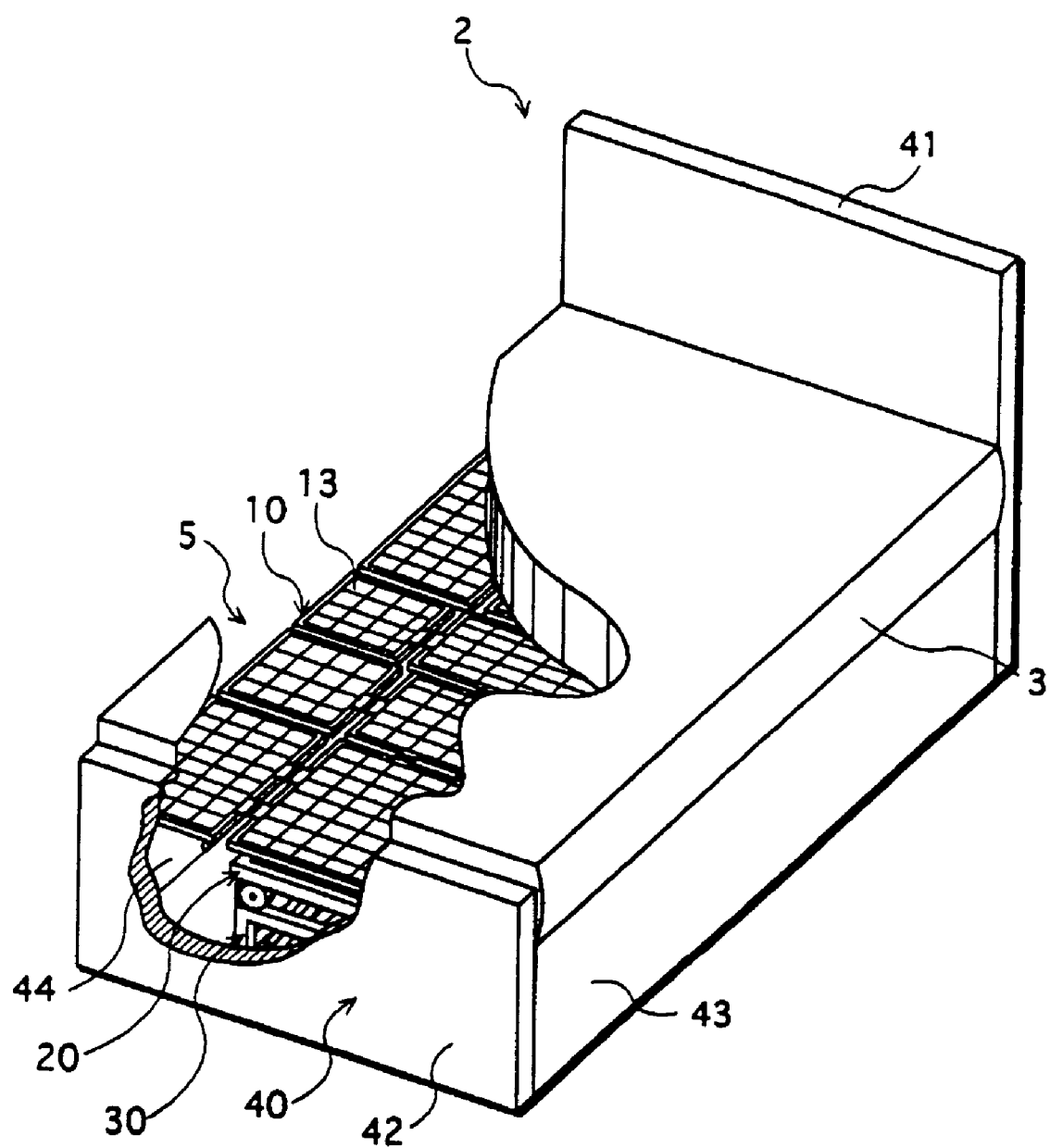
FIG. 13 is a perspective cutaway view of the bed body.

FIG. 13 is a perspective cutaway view of the bed body 2. As illustrated, the bed body 2 includes the bed frame 10, a movable stage 20, a fixed stage 30, and a bedstead 40. The bed frame 10 forms the bed surface 13. The movable stage 20 and the fixed stage 30 serve as the tilt mechanism 5 for moving the bed frame 10. The bedstead 40 encloses the bed frame 10, the movable stage 20, and the fixed stage 30.

FIG. 14 is a perspective view of constructions of the bed frame 10, the movable stage 20, and the fixed stage 30. The bed frame 10, the movable stage 20, and the fixed stage 30 are explained in this order below.

(1) Bed Frame 10

To bend and/or tilt the bed surface 13 and to raise one side of the bed surface 13 when tilting the bed surface 13, the bed frame 10 is constructed as shown in FIG. 14. In detail, the bed frame 10 is divided into three sections that are the right section 12R, the bed section 11, and the left section 12L, in the direction of the width of the bed 1 (Y direction). The bed section 11 is divided into four sections that correspond to the back, buttocks, thighs, and calves of the user 7, in the direction of the length of the bed 1 (X direction). These four sections of the bed section 11 are denoted as the back bed section 11a, a buttock bed section 11b, the thigh bed section 11c, and a calf bed section 11d. Likewise, the right section 12R is divided into four sections that are a back right section 12Ra, a buttock right section 12Rb, a thigh right section 12Rc, and a calf right section 12Rd. The left section 12L is divided into four sections that are a back left section 12La, a buttock left section 12Lb, a thigh left section 12Lc, and a calf left section 12Ld. Note here that the surface of the bed frame 10 (i.e. the bed surface 13) is actually covered with wire mesh as shown in FIG. 13, though such wire mesh is omitted in FIG. 14 for ease of explanation of other construction elements. Also, the back bed section 11a actually has a reinforcing stay which connects opposite sides of a frame structure of the back bed section 11a to reinforce the back bed section 11a, though such a reinforcing stay is omitted in FIG. 14. The same applies to the buttock bed section 11b, the thigh bed section 11c, and the calf bed section 11d. Furthermore, this embodiment describes the case where the bed section 11, the right section 12R, and the left section 12L are shaped like a frame, but they may instead be shaped like a plate.

Figure 15A:
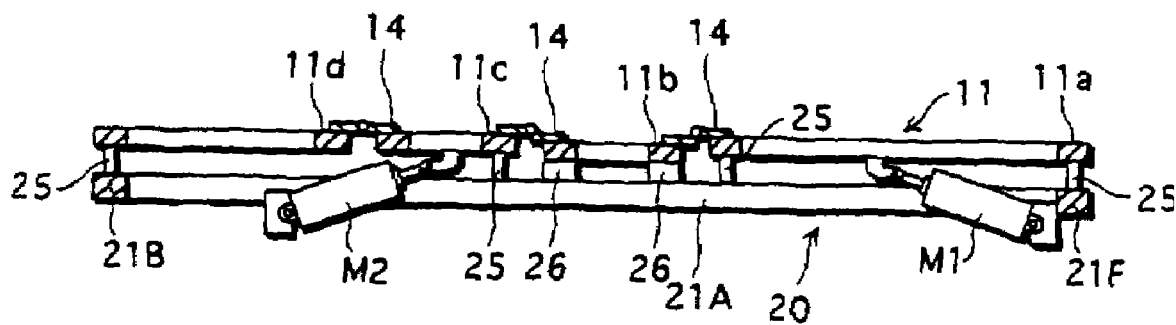
FIGS. 15A and 15B are fragmentary views taken along the line A—A shown in FIG. 14, respectively when the bed frame is in a flat, horizontal position and when a back bed section and a thigh bed section of the bed frame are raised.
Figure 15B:
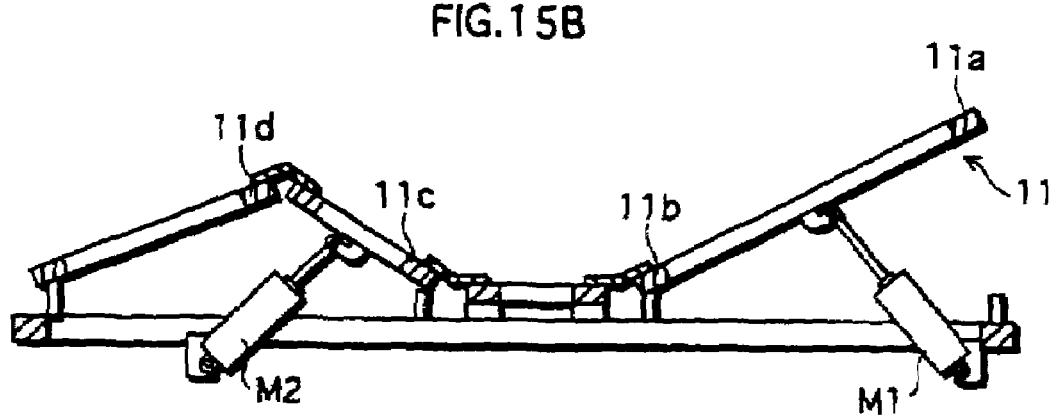

FIG. 15A is a fragmentary view taken along the line A—A shown in FIG. 14, when the bed frame 10 is in a substantially flat, horizontal position. FIG. 15B is a fragmentary view taken along the line A—A shown in FIG. 14, when the bed frame 10 is in a bent position.

The back bed section 11a, the thigh bed section 11c, and the calf bed section 11d are supported by the movable stage 20 with spacers 25 interposed therebetween, so as to be movable away from the movable stage 20.

Meanwhile, the buttock bed section 11b is attached to spacers 26 which are fixed to the movable stage 20, by welding or the like. The buttock bed section 11b is not movable away from the movable stage 20. Thus, the bed frame 10 is fixed to the movable stage 20 at the buttock bed section 11b.

Adjacent sections out of the back bed section 11a, the buttock bed section 11b, the thigh bed section 11c, and the calf bed section 11d are connected by hinges 14. An axis of each of the hinges 14 extends in the direction of the width of the bed 1. Accordingly, the back bed section 11a can pivot up and down about the axis of the hinge 14 which is situated between the back bed section 11a and the buttock bed section 11b. Likewise, the thigh bed section 11c can pivot up and down about the axis of the hinge 14 which is situated between the buttock bed section 11b and the thigh bed section 11c, and the calf bed section 11d can pivot up and down about the axis of the hinge 14 which is situated between the thigh bed section 11c and the calf bed section 11d.

The actuator M1 serves to raise the back bed section 11a from the horizontal position and return it to the horizontal position. Meanwhile, the actuator M2 serves to raise the thigh bed section 11c and the calf bed section 11d from the horizontal position and return them to the horizontal position. The actuators M1 and M2 are controlled by the control unit 100.

Figure 16A:
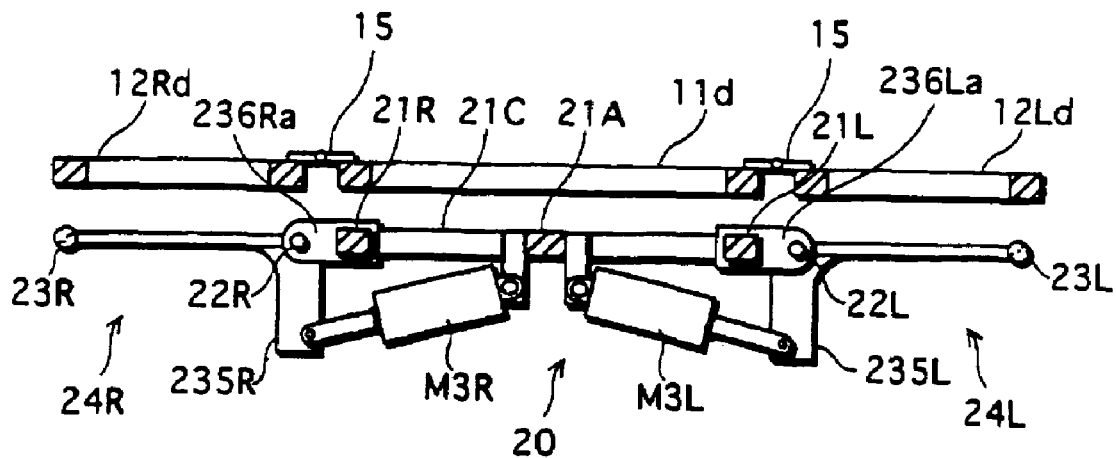
FIGS. 16A and 16B are fragmentary views taken along the line B—B shown in FIG. 14, respectively when the bed frame is in a flat, horizontal position and when a left section of the bed frame is being raised.
Figure 16B:
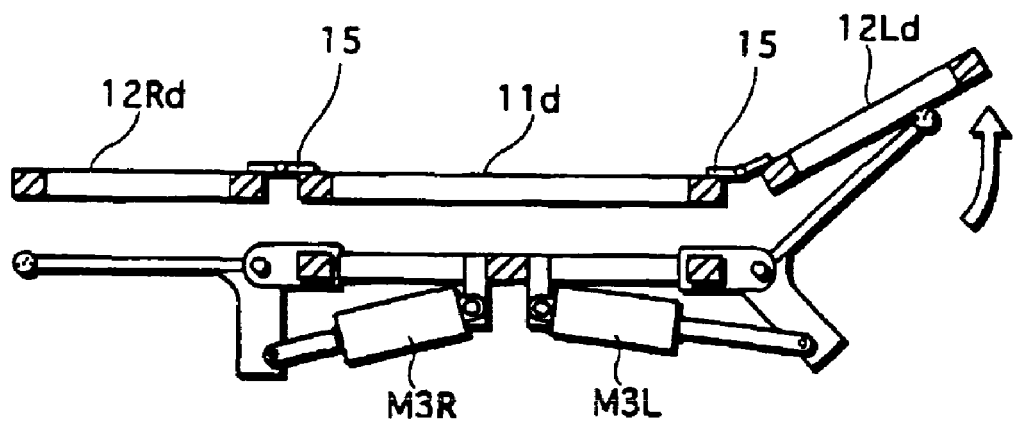

FIG. 16A is a fragmentary view taken along the line B—B shown in FIG. 14, when the bed frame 10 is in a substantially flat, horizontal position. FIG. 16B is a fragmentary view taken along the line B—B shown in FIG. 14, when the left section 12L of the bed frame 10 is raised.

As shown in FIGS. 14 and 16, the calf right section 12Rd and the calf left section 12Ld are connected respectively to the right and left sides of the calf bed section 11d by hinges 15. An axis of each of the hinges 15 extends in the direction of the length of the bed 1. Accordingly, the calf right section 12Rd can pivot up and down about the axis of the hinge 15 which is situated between the calf right section 12Rd and the calf bed section 11d. Likewise, the calf left section 12Ld can pivot up and down about the axis of the hinge 15 which is situated between the calf left section 12Ld and the calf bed section 11d. The other sections have the same construction. In more detail, the back right section 12Ra and the back left section 12La are connected respectively to the right and left sides of the back bed section 11a by hinges 15. The buttock right section 12Rb and the buttock left section 12Lb are connected respectively to the right and left sides of the buttock bed section 11b by hinges 15. The thigh right section 12Rc and the thigh left section 12Lc are connected respectively to the right and left sides of the thigh bed section 11c by hinges 15. The actuator M3R serves to raise the right section 12R from the horizontal position and return it to the horizontal position. The actuator M3L serves to raise the left section 12L from the horizontal position and return it to the horizontal position. The actuators M3R and M3L are controlled by the control unit 100.

(2) Movable Stage 20

Figure 17:
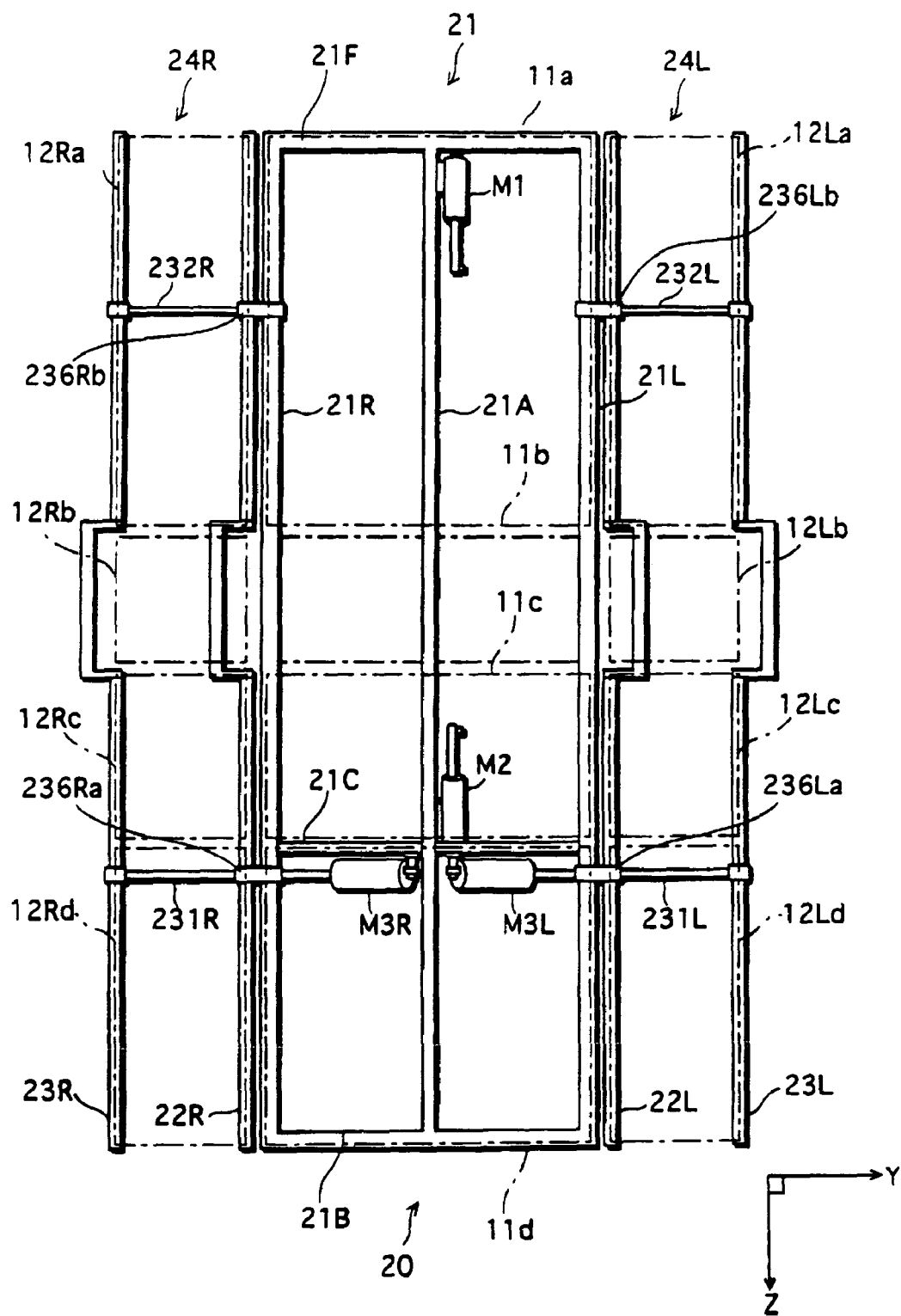
FIG. 17 is a top view of the movable stage.
Figure 18:
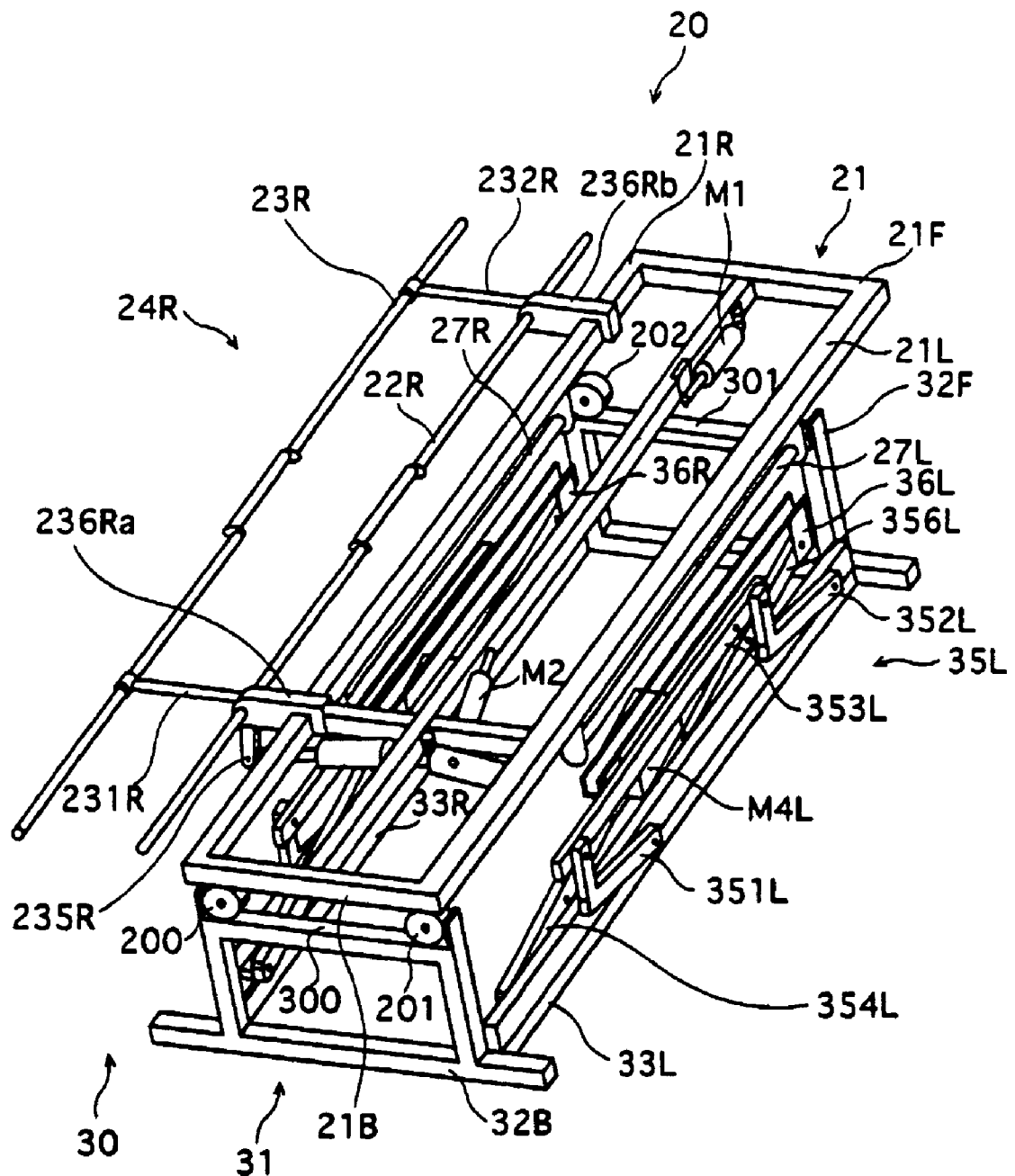
FIG. 18 is a perspective view of the movable stage.

FIG. 17 is a top view of the movable stage 20. FIG. 18 is a perspective view of the movable stage 20. In FIG. 17, the bed frame 10 is indicated with dashed lines. In FIG. 18, only parts of the movable stage 20 that correspond to the right section 12R and the bed section 11 of the bed frame 10 are shown while omitting parts corresponding to the left section 12L, for ease of explanation.

As shown in FIGS. 17 and 18, the movable stage 20 is made up of a bed section supporter 21, a right section supporter 24R, and a left section supporter 24L. The bed section supporter 21 has a rectangular shape with its longer sides running in the direction of the length of the bed 1, and supports the bed section 11 of the bed frame 10. The right section supporter 24R supports and raises the right section 12R of the bed frame 10. The left section supporter 24L supports and raises the left section 12L of the bed frame 10.

The bed section supporter 21 is formed by one pair of side members 21R and 21L and one pair of end members 21F and 21B. The side members 21R and 21L run in the direction of the length of the bed 1 in parallel with each other. The end members 21F and 21B run in the direction of the width of the bed 1 in parallel with each other, and connect both ends of the side members 21R and 21L. A reinforcing member 21A connects substantially center parts of the end members 21F and 21B. A reinforcing member 21C connects the side members 21R and 21L and the reinforcing member 21A. The reinforcing members 21A and 21C serve to reinforce the bed section supporter 21.

The actuator M1 is attached to one part of the reinforcing member 21A which corresponds to the back bed section 11a. An end of a rod of the actuator M1 is connected to the aforementioned reinforcing stay (not illustrated) of the back bed section 11a. Meanwhile, the actuator M2 is attached to one part of the reinforcing member 21A which corresponds to the thigh bed section 11c and the calf bed section 11d. An end of a rod of the actuator M2 is connected to the thigh bed section 11c.

Figure 19:
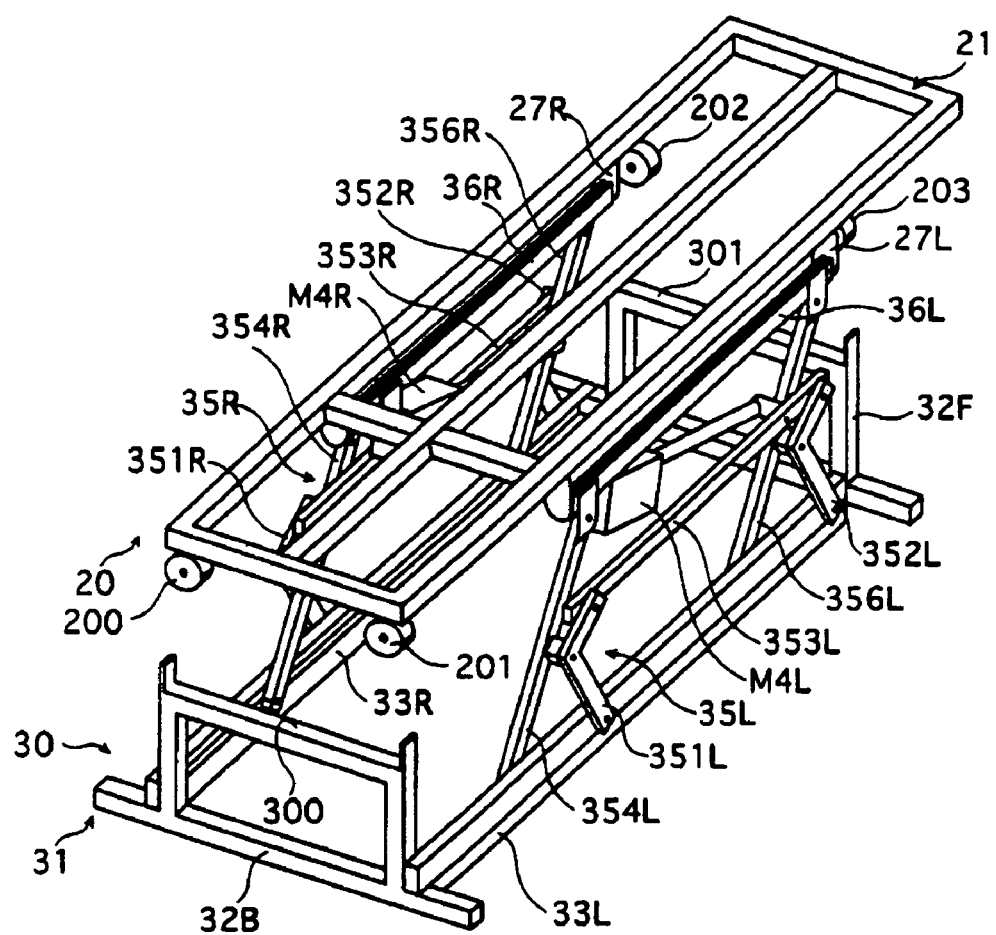
FIG. 19 is a perspective view of the fixed stage.

Rollers 200, 201, 202, and 203 (the roller 203 is hidden under the side member 21L in FIG. 18 but is shown in FIG. 19) are provided to the bed section supporter 21. The rollers 200, 201, 202, and 203 are slidable on upper faces 300 of base members 32F and 32B of the fixed stage 30, in the direction of the width of the bed 1.

The right section supporter 24R has one pair of bars 22R and 23R which run in the direction of the length of the bed 1 and one pair of bars 231R and 232R which connect the bars 22R and 23R, so as to assume the shape of a ladder. The bar 22R is connected to the side member 21R of the bed section supporter 21 by connectors 236Ra and 236Rb which are fixed to the side member 21R. Also, the left section supporter 24L has one pair of bars 22L and 23L which run in the direction of the length of the bed 1 and one pair of bars 231L and 232L which connect the bars 22L and 23L, so as to assume the shape of a ladder. The bar 22L is connected to the side member 21L of the bed section supporter 21 by connectors 236La and 236Lb which are fixed to the side member 21L.

The bar 22R is supported rotatably by the connectors 236Ra and 236Rb, whilst the bar 22L is supported rotatably by the connectors 236La and 236Lb. This allows the right section supporter 24R and the left section supporter 24L to pivot about the bars 22R and 22L respectively.

Also, a projection 235R which projects downward is fixed to the bar 22R near a part that is connected with the connector 236Ra, and a projection 235L which projects downward is fixed to the bar 22L near a part that is connected with the connector 236La (see FIG. 16 etc.). An end of the projection 235R is connected with one end of the rod of the actuator M3R, and an end of the projection 235L is connected with one end of the rod of the actuator M3L.

The actuators M3R and M3L are attached to the reinforcing member 21C, as shown in FIG. 16. This being so, when the rod of the actuator M3R extends, the right section supporter 24R rises by pivoting about the bar 22R. This pushes up the right section 12R of the bed frame 10. Likewise, when the rod of the actuator M3L extends, the left section supporter 24L rises by pivoting about the bar 22L. This pushes up the left section 12L of the bed frame 10.

Stage bars 27R and 27L are provided beneath the side members 21R and 21L respectively, as shown in FIG. 18. The size of the stage bars 27R and 27L is such that the stage bars 27R and 27L can exactly fit in respective grooves of U-shaped stage bar holders 36R and 36L provided on the fixed stage 30. When raising the movable stage 20 (the bed frame 10), the stage bar holders 36R and 36L are raised. This pushes up the stage bars 27R and 27L in a state where the stage bars 27R and 27L are fit respectively in the grooves of the stage bar holders 36R and 36L. As a result, the movable stage 20 is raised.

(3) Fixed Stage 30

FIG. 19 is a perspective view of the construction of the fixed stage 30.

As shown in the drawing, the fixed stage 30 includes a base 31 and elevators 35R and 35L. The base 31 supports the movable stage 20. The elevators 35R and 35L raise/lower or tilt the movable stage 20.

The base 31 is made up of one pair of base members 32F and 32B and one pair of connectors 33R and 33L. The base members 32F and 32B are arranged in the direction of the length of the bed 1 with a space therebetween. The connectors 33R and 33L connect the base members 32F and 32B to each other. The connectors 33R and 33L each have a slide groove which is shaped like the Japanese katakana letter "コ" and faces the other connector. Lower ends of arms 354R and 356R are inserted in the slide groove of the connector 33R so as to be slidable in the direction of the length of the bed 1. Also, lower ends of arms 354L and 356L are inserted in the slide groove of the connector 33L so as to be slidable in the direction of the length of the bed 1.

The elevator 35R is positioned between the base members 32F and 32b on the right side of the base 31, whereas the elevator 35L is positioned between the base members 32F and 32B on the left side of the base 31. To raise or lower the movable stage 20, both of the elevators 35R and 35L operate. To tilt the movable stage 20, only one of the elevators 35R and 35L operates. FIG. 19 shows a situation where the movable stage 20 is raised.

The elevators 35R and 35L are each constructed by a parallelogram mechanism which employs a longitudinal sliding function. This is explained in more detail below.

As mentioned earlier, the lower ends of the arms 354R and 356R are inserted in the slide groove of the connector 33R so as to be slidable in the direction of the length of the bed 1, and the lower ends of the arms 354L and 356L are inserted in the slide groove of the connector 33L so as to be slidable in the direction of the length of the bed 1. Meanwhile, the upper ends of the arms 354R and 356R are connected to both ends of the stage bar holder 36R, and the upper ends of the arms 354L and 356L are connected to both ends of the stage bar holder 36L. Also, center parts of the arms 354R and 356R are connected respectively to bent parts of inverted-L-shaped cranks 351R and 352R. One end of each of the cranks 351R and 352R is linked to an outer side face of the connector 33R. The other ends of the cranks 351R and 352R are linked to each other via a link 353R. Likewise, center parts of the arms 354L and 356L are connected respectively to bent parts of inverted-L-shaped cranks 351L and 352L. One end of each of the cranks 351L and 352L is linked to an outer side face of the connector 33L. The other ends of the cranks 351L and 352L are linked to each other via a link 353L. Furthermore, the actuator M4R is attached to the stage bar holder 36R, and the actuator M4L is attached to the stage bar holder 36L. One end of a rod of the actuator M4R is connected to the link 353R, whereas one end of a rod of the actuator M4L is connected to the link 353L.

In such a parallelogram mechanism, when the rod of the actuator M4R and the rod of the actuator M4L extend/compress, the cranks 351R and 352R make circular motion about the connecting parts with the connector 33R, and the cranks 351L and 352L make circular motion about the connecting parts with the connector 33L. In sync with the circular motion of the cranks 351R and 352R, the lower ends of the arms 354R and 356R slide along the groove of the connector 33R. Also, in sync with the circular motion of the cranks 351L and 352L, the lower ends of the arms 354L and 356L slide along the groove of the connector 33L. This causes the arms 354R and 356R to swing about their connecting parts with the cranks 351R and 352R, and the arms 354L and 356L to swing about their connecting parts with the cranks 351L and 352L. As a result, the stage bar holders 36R and 36L move up and down. Thus, the movable stage 20 is raised and lowered via the stage bars 27R and 27L.

When tilting the movable stage 20 to one side, on the other hand, only one of the elevators 35R and 35L operates as mentioned above. To tilt the movable stage 20 to the right, for instance, the elevator 35L operates to raise the left part of the movable stage 20. In this case, the elevator 35R does not operate. Accordingly, the stage bar 27R and the stage bar holder 36R remain separated from each other. In other words, the rollers 200 and 202 of the movable stage 20 are in contact with the upper faces 300 of the base members 32B and 32F of the fixed stage 30, respectively. This being so, as the left part of the movable stage 20 rises, the rollers 200 and 202 slide leftward on the upper faces 300.

To tilt the movable stage 20 to the left, on the other hand, the elevator 35R operates to raise the right part of the movable stage 20. In this case, as the left part of the movable stage 20 rises, the rollers 201 and 203 of the movable stage 20 slide rightward on the upper faces 300. These actuators M4R and M4L are controlled by the control unit 100.

(4) Movements of the Bed 1

FIG. 20 shows movements of the bed 1 when the user 7 is turned on his or her right side by the tilt mechanism 5.

Figure 20A:
FIG. 20 shows a representation of a change of bed positions when an operation of tilting the bed surface to the right is performed to turn the user on his or her right side.
Figure 20B:
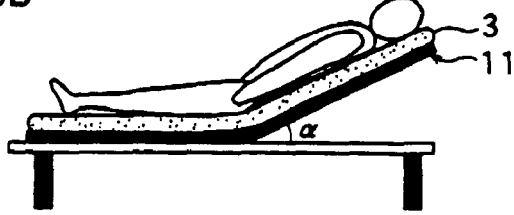
Figure 20C:
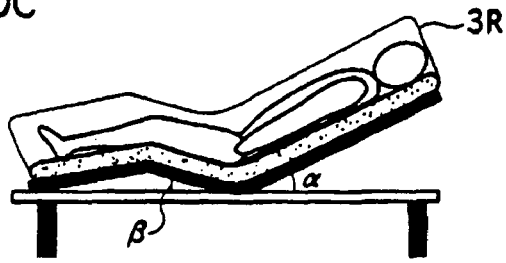
Figure 20D:
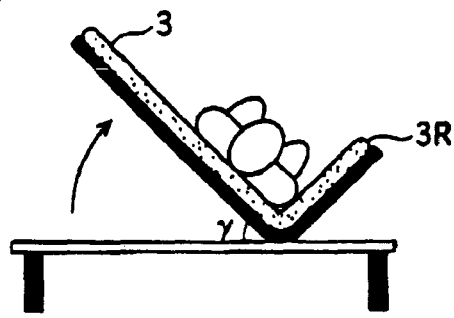

Initially, the bed surface 13 (the mattress 3) is in a flat, horizontal position (FIG. 20A). Then the back bed section 11a is raised by an angle α (FIG. 20B), and the thigh bed section 11c is raised by an angle β to bend up the knees of the user 7. Also, the right section 12R (a right part 3R of the mattress 3) is raised upright (FIG. 20C).

After this, the bed surface 13 is tilted to the right by an angle γ, to turn the user 7 on his or her right than when the user 7 is awake, in order to keep the user 7 from feeling stress during sleep.

(2) The above embodiment describes the case where the bed surface 13 is tilted in a state where the bed section 11 is bent and the right section 12R or the left section 12L is raised. This has an advantage of providing the sense of security to the user 7. However, an operation of turning the user 7 is not limited to this. According to circumstances, the invention may equally be applied to adjustable beds which tilt the bed surface in a flat state.

(3) The above embodiment describes the case where each actuator such as M1 is a motor-driven actuator with a built-in direct-current servomotor, but any actuator having a linearly extendable rod may be used. As a motor-driven actuator, an actuator driven by a stepping motor may be used.

Also, the primary drive for bending/tilting the bed surface 13 is not limited to an actuator. For example, the bed surface 13 may be bent/tilted by employing an air mattress having a plurality of air sacs and individually supplying/ejecting air to/from each air sac.

Also, such an air mattress which exerts a tilt function through the use of a plurality of air sacs may itself be used as the bed body in the adjustable bed of the invention.

(4) The above embodiment describes an example where the invention is used for a turn assisting bed, but this is not a limit for the invention, which may equally be used as an apnea syndrome treatment bed. When the invention is used as an apnea syndrome treatment bed, it is desirable to add a display for displaying a sleep depth analysis result obtained by the control unit 100 and/or a printer for printing out the analysis result.

Although the present invention has been fully described by way of examples with reference to the accompanying drawings, it is to be noted that various changes and modifications will be apparent to those skilled in the art.

Therefore, unless such changes and modifications depart from the scope of the present invention, they should be construed as being included therein.

What is claimed is:

1. An adjustable bed system comprising:
a bed adapted to move a body of a person lying on the bed into a bent position by elevating the upper body and bending the knees;
a tilt unit adapted to tilt the bed laterally while the bed is in a bent position;
a judgment unit adapted to determine the sleep stage of a person lying on the bed; and
a control unit adapted to control the tilt unit in response to a sleep stage judgment made by the judgment unit.

2. The adjustable bed of claim 1,
wherein the judgment unit determines whether the person is in REM sleep, and
the control unit causes the tilt unit to tilt the bed, if the judgment unit determines that the person is in REM sleep.

3. The adjustable bed of claim 1,
wherein the judgment unit determines a depth of sleep of the person, and
the control unit causes the tilt unit to tilt the bed, if the judgment unit determines that the person is in slow wave sleep.

4. The adjustable bed of claim 2,
wherein the judgment unit determines a depth of sleep of the person, and
the control unit causes the tilt unit to tilt the bed, if the judgment unit determines that the person is in slow wave sleep.

5. The adjustable bed of claim 1,
wherein the control unit prohibits the tilt unit from performing a tilt operation within a predetermined time period from a preceding tilt operation, irrespective of the depth of sleep of the person.

6. The adjustable bed of claim 2,
wherein the control unit prohibits the tilt unit from performing a tilt operation within a predetermined time period from a preceding tilt operation, irrespective of the depth of sleep of the person.

7. The adjustable bed of claim 3,
wherein the control unit prohibits the tilt unit from performing a tilt operation within a predetermined time period from a preceding tilt operation, irrespective of the depth of sleep of the person.

8. The adjustable bed of claim 4,
wherein the control unit prohibits the tilt unit from performing tilt operation within a predetermined time period from a preceding tilt operation, irrespective of the depth of sleep of the person.

* * * * *